United States Patent
Wilson et al.

(10) Patent No.: US 9,688,630 B2
(45) Date of Patent: Jun. 27, 2017

(54) 3,3'-DISUBSTITUTED INDOLINES AS INHIBITORS OF CHOLESTEROL ESTER TRANSFER PROTEIN

(71) Applicant: Merck Sharp & Dohme Corp., Rahway, NJ (US)

(72) Inventors: Jonathan E. Wilson, South Orange, NJ (US); Petr Vachal, Summit, NJ (US); Ravi Kurukulasuriya, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/028,306

(22) PCT Filed: Oct. 6, 2014

(86) PCT No.: PCT/US2014/059214
§ 371 (c)(1),
(2) Date: Apr. 8, 2016

(87) PCT Pub. No.: WO2015/054088
PCT Pub. Date: Apr. 16, 2015

(65) Prior Publication Data
US 2016/0355474 A1    Dec. 8, 2016

Related U.S. Application Data

(60) Provisional application No. 61/889,120, filed on Oct. 10, 2013.

(51) Int. Cl.
| | | |
|---|---|---|
| *C07D 491/107* | (2006.01) |
| *C07D 417/06* | (2006.01) |
| *C07D 413/10* | (2006.01) |
| *C07D 405/12* | (2006.01) |
| *C07D 403/10* | (2006.01) |
| *C07D 401/04* | (2006.01) |
| *C07D 401/06* | (2006.01) |
| *C07D 401/10* | (2006.01) |
| *A61K 31/5377* | (2006.01) |
| *A61K 31/4439* | (2006.01) |
| *A61K 31/454* | (2006.01) |
| *A61K 31/427* | (2006.01) |
| *A61K 31/404* | (2006.01) |
| *C07D 209/12* | (2006.01) |
| *A61K 45/06* | (2006.01) |
| *C07D 209/10* | (2006.01) |
| *C07D 209/24* | (2006.01) |
| *C07D 209/14* | (2006.01) |
| *C07D 209/18* | (2006.01) |

(52) U.S. Cl.
CPC .......... *C07D 209/12* (2013.01); *A61K 31/404* (2013.01); *A61K 31/427* (2013.01); *A61K 31/4439* (2013.01); *A61K 31/454* (2013.01); *A61K 31/5377* (2013.01); *A61K 45/06* (2013.01); *C07D 209/10* (2013.01); *C07D 209/14* (2013.01); *C07D 209/18* (2013.01); *C07D 209/24* (2013.01); *C07D 401/04* (2013.01); *C07D 401/06* (2013.01); *C07D 401/10* (2013.01); *C07D 403/10* (2013.01); *C07D 405/12* (2013.01); *C07D 413/10* (2013.01); *C07D 417/06* (2013.01); *C07D 491/107* (2013.01)

(58) Field of Classification Search
CPC .. C07D 209/12; C07D 209/10; C07D 209/14; C07D 209/18; C07D 209/24; C07D 401/04; C07D 401/06; C07D 401/10; C07D 403/10; C07D 405/12; C07D 413/10; C07D 417/06; C07D 491/107; A61K 31/404; A61K 31/427; A61K 31/4439; A61K 31/454; A61K 31/5377
See application file for complete search history.

(56) References Cited

U.S. PATENT DOCUMENTS

| | | | |
|---|---|---|---|
| 7,652,049 B2 | 1/2010 | Ali et al. |
| 7,737,295 B2 | 6/2010 | Ali et al. |
| 7,781,426 B2 | 8/2010 | Ali et al. |
| 7,910,592 B2 | 3/2011 | Ali et al. |
| 7,915,271 B2 | 3/2011 | Ali et al. |
| 8,293,721 B2 | 10/2012 | Hunt et al. |
| 8,334,290 B2 | 12/2012 | Ali et al. |
| 8,436,028 B2 | 5/2013 | Hunt et al. |
| 8,445,480 B2 | 5/2013 | Hunt et al. |
| 8,486,983 B2 | 7/2013 | Sheth et al. |
| 8,865,707 B2 | 10/2014 | Ali et al. |
| 8,871,738 B2 | 10/2014 | Shao et al. |
| 9,126,976 B2 | 9/2015 | Anand et al. |
| 9,221,834 B2 | 12/2015 | Lu et al. |
| 9,353,101 B2 | 5/2016 | Acton, III et al. |

(Continued)

FOREIGN PATENT DOCUMENTS

| | | |
|---|---|---|
| WO | 2006032987 A1 | 3/2006 |
| WO | 2015094932 A1 | 6/2015 |

OTHER PUBLICATIONS

International Search Report and Written Opinion for PCT/US2014/059214, mailed Dec. 23, 2014; 8 pages.

(Continued)

*Primary Examiner* — Rebecca Anderson
(74) *Attorney, Agent, or Firm* — Eric A. Meade; Catherine D. Fitch

(57) ABSTRACT

3,3'-Disubstituted indoline compounds, including pharmaceutically acceptable salts of the compounds, are CETP inhibitors and are useful for raising HDL-cholesterol, reducing LDL-cholesterol, and for treating or preventing atherosclerosis.

15 Claims, No Drawings

(56) References Cited

U.S. PATENT DOCUMENTS

| | | |
|---|---|---|
| 9,376,408 B2 | 6/2016 | Shao et al. |
| 2006/0030613 A1 | 2/2006 | Conte-Mayweg et al. |
| 2006/0270675 A1 | 11/2006 | Groneberg et al. |
| 2007/0265304 A1 | 11/2007 | Rano et al. |
| 2015/0342931 A1 | 12/2015 | Ondeyka et al. |
| 2016/0185784 A1 | 6/2016 | Liu et al. |

OTHER PUBLICATIONS

Pubchem 6P-094, Compound Summary for CID 4301954, U.S. National Library of Medicine, Sep. 14, 2005, retrieved from internet: ,URL: https://pubchem.ncbi.nlm.gov/compound/4301954#section=Top>.

Wilson, J.E., et al., Discovery of Novel Indoline Cholesterol Ester Transfer Protein Inhibitors (CETP) through a Structure-Guided Approach, ACS Medicinal Chemistry Letters, Jan. 2016, pp. 261-265, vol. 7(3).

3,3'-DISUBSTITUTED INDOLINES AS INHIBITORS OF CHOLESTEROL ESTER TRANSFER PROTEIN

CROSS-REFERENCE TO RELATED APPLICATIONS

This application is a U.S. National Phase application under 35 U.S.C. §371 of PCT/US2014/059214, filed Oct. 6, 2014, which claims priority from U.S. provisional application no. 61/889,120 filed Oct. 10, 2013.

FIELD OF THE INVENTION

This invention relates to chemical compounds that inhibit cholesterol ester transfer protein (CETP) and that are expected to have utility in raising HDL-C, lowering LDL-C, and in the treatment and prevention of atherosclerosis.

BACKGROUND OF THE INVENTION

Atherosclerosis and its clinical consequences, including coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA reductase inhibitors, especially the statins, in reducing coronary events is based on the reduction of circulating low density lipoprotein cholesterol (LDL-C), levels of which correlate directly with an increased risk for atherosclerosis. More recently, epidemiologic studies have demonstrated an inverse relationship between high density lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoprotein and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120(3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering LDL-C.

Despite the significant therapeutic advance that statins such as simvastatin and atorvastatin represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin provides an effective therapy for raising HDL-C but suffers from patient compliance issues, due in part to side effects such as flushing. Drugs that inhibit CETP (CETP inhibitors) have been under development with the expectation that they will effectively raise HDL cholesterol levels and also reduce the incidence of atherosclerosis in patients. Torcetrapib was the first drug that was tested in a long-term outcomes clinical trial. The clinical trial of torcetrapib was terminated early due to a higher incidence of mortality in patients to whom torcetrapib and atorvastatin were administered concomitantly compared with patients who were treated with atorvastatin alone. The cause of the increased mortality is not completely understood, but it is not believed to be associated with the CETP inhibiting effects of the drug. Dalcetrapib was recently tested in a Phase III outcomes trial, which was terminated early because the interim data did not show a clinical benefit. There were no safety issues detected for dalcetrapib.

Anacetrapib is currently the only CETP inhibitor being tested in a large scale Phase III clinical outcomes trial. Data from the recently completed DEFINE Phase II/III trial of anacetrapib are promising. Patients who were treated with anacetrapib along with baseline statin therapy showed an increase of HDL-C of 138% and a decrease of LDL-C of 40% compared with patients who were treated with just a statin. See: *N. Engl. J. Med.* 2010: 363: 2406-15. The DEFINE study was not carried out on a large enough scale to serve as a pivotal outcomes trial, but the data in the DEFINE trial were sufficient to indicate that an increase in mortality for patients treated with anacetrapib is unlikely. Additional drug candidates are in development. Evacetrapib currently appears to be the next CETP inhibitor that will proceed to a Phase III outcomes trial. Additional compounds are being sought that may have properties that are advantageous compared with the CETP inhibitors that have so far been studied or are currently being studied. Such properties may include, for example, higher potency, reduced off-target activity, better pharmacodynamics, higher bioavailability, or a reduced food effect compared with many of the highly lipophilic compounds that have so far been studied. "Food effect" refers to the variability in exposure to the active drug that occurs depending on when the patient had last eaten, whether or not the drug is administered with food, and the fat content of the food.

SUMMARY OF THE INVENTION

The compound of Formula I, or a pharmaceutically acceptable salt thereof, is a potent CETP inhibitor, having the utilities described below:

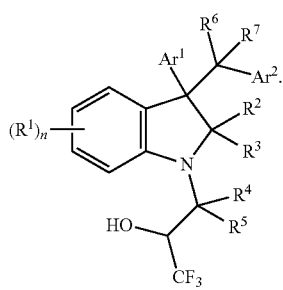

In Formula I, 1-2 carbon atoms in the phenyl ring are optionally replaced with 1-2 heteroatoms selected from NH, S, and O to create a 5-6 membered heteroaromatic ring.

Each $R^1$ is independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^9R^{10}$, —$CO_2R^8$, —$C(O)NR^9R^{10}$, —$SO_2NR^9R^{10}$, HET(1), phenyl, or $C_{3-6}$ cycloalkyl optionally having 1-2 double bonds, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are each optionally substituted with 1-9 halogens, and wherein HET(1), phenyl, and $C_{3-6}$ cycloalkyl optionally having 1-2 double bonds are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, and —$OC_2$-$C_3$ alkynyl are each optionally substituted with 1-7 halogens;

$R^2$, $R^3$, $R^4$, $R^5$, $R^6$, and $R^7$ are each independently H, —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^9R^{10}$, —$CO_2R^8$, —$C(O)NR^9R^{10}$, —$SO_2NR^9R^{10}$, HET(1), phenyl, or $C_{3-6}$ cycloalkyl optionally having 1-2 double bonds, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are each optionally substituted with 1-9 halogens, and wherein HET(1), phenyl, and $C_{3-6}$ cycloalkyl optionally having 1-2 double bonds, are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, and —$OC_2$-$C_3$ alkynyl are each optionally substituted with 1-7 halogens;

$R^8$ is H or —$C_{1-5}$alkyl optionally substituted with 1-9 halogens;

$R^9$ and $R^{10}$ are each independently H, —$C_1$-$C_5$ alkyl, —$C_2$-$C_5$ alkenyl, —$C_2$-$C_5$ alkynyl, phenyl, $C_{3-6}$ cycloalkyl optionally having 1-2 double bonds, or HET(1), wherein phenyl, $C_{3-6}$ cycloalkyl optionally having 1-2 double bonds, and HET(1) are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$alkynyl, and —$OC_2$-$C_3$ alkynyl are each optionally substituted with 1-7 halogens;

HET(1) is a 3-7 membered heterocyclic or heteroaromatic ring having 1-4 heteroatoms or heteroatom groups which are each independently N, NH, O, S, S(O), or $S(O)_2$ and optionally having 1-3 double bonds;

$Ar^1$ and $Ar^2$ are each independently phenyl, naphthyl, $C_{3-6}$ cycloalkyl optionally having 1-2 double bonds, or HET(1), wherein $Ar^1$ and $Ar^2$ are each optionally substituted with 1-5 substituents which are independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^9R^{10}$, —$CO_2R^8$, —$SO_2C_1$-$C_5$alkyl, —$C(O)C_1$-$C_5$ alkyl, —$C(O)NR^9R^{10}$, —$SO_2NR^9R^{10}$, or —$NR^9C(O)NR^9R^{10}$, and optionally 1-2 substituents which are phenyl, $C_{3-6}$ cycloalkyl optionally having 1-2 double bonds, HET (1), or HET(2), wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —$SO_2C_1$-$C_5$alkyl, and —$C(O)C_1$-$C_5$ alkyl are optionally substituted with 1-9 halogens, and wherein when phenyl, $C_{3-6}$ cycloalkyl optionally having 1-2 double bonds, HET(1), and HET(2) are substituents on $Ar^1$ and $Ar^2$, then phenyl, $C_{3-6}$ cycloalkyl optionally having 1-2 double bonds, HET(1), and HET(2) are optionally substituted with 1-3 substituent groups which are each independently halogen, —OH, —CN, —$NR^9R^{10}$, —$CO_2R^8$, —$C_1$-$C_3$ alkyl, or —$OC_1$-$C_3$ alkyl, wherein —$C_1$-$C_3$ alkyl and —$OC_1$-$C_3$ alkyl are optionally substituted with 1-7 halogens and optionally with 1-2 groups which are —OH, halogen, —CN, —$NR^9R^{10}$, and —$CO_2R^8$;

HET(2) is a bicyclic or spirocyclic heterocycle having two 3-6 membered heterocyclic rings which are fused or are connected through a single carbon atom to make a spirocyclic connection, wherein HET(2) has 2-4 heteroatoms or heteroatom groups which are O, S, $S(O)_2$, N, or NH, and optionally comprises 1-2 double bonds; and n is 0 or an integer from 1-4.

In the compound(s) of Formula I, and in subgroups and other embodiments of the invention, alkyl groups and substituents based on alkyl groups, such as alkoxy, may be linear or branched unless otherwise indicated.

In general, references to the compound(s) of formula I are meant to also include subsets of compounds of formula I as may be defined herein, and also are meant to include the specific numbered examples provided herein. In further embodiments of the invention that are defined herein, the defined substituent groups may have alternative values independent of one another and can be varied in different embodiments independently of one another. Such embodiments include pharmaceutically acceptable salts when such salts are possible.

DETAILED DESCRIPTION OF THE INVENTION

In some embodiments of the invention, the phenyl ring in Formula I does not have optional heteroatoms, so that it is always phenyl.

In some embodiments of the invention, each $R^1$ is independently —$C_1$-$C_5$ alkyl, —$OC_1$-$C_5$ alkyl, —OH, halogen, —CN, —$NR^9R^{10}$, —$CO_2R^8$, —$C(O)NR^9R^{10}$, —$SO_2NR^9R^{10}$, phenyl, or $C_{3-6}$ cycloalkyl, wherein —$C_1$-$C_5$ alkyl and —$OC_1$-$C_5$ alkyl are each optionally substituted with 1-9 halogens, and wherein phenyl and $C_{3-6}$ cycloalkyl are each optionally substituted with 1-3 groups which are independently halogen, —$C_1$-$C_3$ alkyl, or —$OC_1$-$C_3$ alkyl, wherein —$C_1$-$C_3$ alkyl and —$OC_1$-$C_3$ are each optionally substituted with 1-7 halogens.

In some embodiments of the invention, $R^2$, $R^3$, $R^4$, $R^5$, $R^6$, and $R^7$ are each independently H, —$C_1$-$C_5$ alkyl, —$OC_1$-$C_5$ alkyl, —OH, halogen, —CN, —$NR^9R^{10}$, —$CO_2R^8$, —$C(O)$ NR$^9$R$^{10}$, or —SO$_2$NR$^9$R$^{10}$, wherein —C$_1$-C$_5$ alkyl and —OC$_1$-C$_5$ alkyl are each optionally substituted with 1-9 halogens.

In some embodiments of the invention, R$^8$ is H or —C$_{1-5}$ alkyl optionally substituted with 1-9 halogens.

In some embodiments of the invention, R$^9$ and R$^{10}$ are each independently H, —C$_1$-C$_5$ alkyl, phenyl, C$_{3-6}$ cycloalkyl, or HET(1), wherein phenyl, C$_{3-6}$ cycloalkyl, and HET(1) are optionally substituted with 1-3 substituent groups which are each independently halogen, —C$_1$-C$_3$ alkyl, or —OC$_1$-C$_3$ alkyl, wherein —C$_1$-C$_3$ alkyl and —OC$_1$-C$_3$ alkyl are each optionally substituted with 1-7 halogens.

In some embodiments of the invention, HET(1) is a 3-7 membered heterocyclic or heteroaromatic ring having 1-4 heteroatoms or heteroatom groups which are each independently N, NH, O, S, S(O), or S(O)$_2$ and optionally having 1-3 double bonds.

In some embodiments of the invention, Ar$^1$ and Ar$^2$ are each independently phenyl, C$_{3-6}$ cycloalkyl, or HET(1), wherein Ar$^1$ and Ar$^2$ are each optionally substituted with 1-5 substituents which are independently —C$_1$-C$_3$ alkyl, —OC$_1$-C$_3$alkyl, —OH, halogen, —CN, —NR$^9$R$^{10}$, —CO$_2$R$^8$, —SO$_2$C$_1$-C$_5$alkyl, —C(O)C$_1$-C$_5$ alkyl, —C(O)NR$^9$R$^{10}$, —SO$_2$NR$^9$R$^{10}$, or —NR$^9$C(O)NR$^9$R$^{10}$, and optionally one substituent which is phenyl, C$_{3-6}$ cycloalkyl, HET(1), or HET(2), wherein —C$_1$-C$_3$alkyl, —OC$_1$-C$_3$ alkyl, —SO$_2$C$_1$-C$_5$alkyl, and —C(O)C$_1$-C$_5$ alkyl are optionally substituted with 1-7 halogens, and wherein when phenyl, C$_{3-6}$ cycloalkyl, HET(1), and HET(2) are substituents on Ar$^1$ and Ar$^2$, then phenyl, C$_{3-6}$ cycloalkyl, HET(1), and HET(2) are optionally substituted with 1-3 substituent groups which are each independently halogen, —OH, —CN, —NR$^9$R$^{10}$, —CO$_2$R$^8$, —C$_1$-C$_3$ alkyl, or —OC$_1$-C$_3$ alkyl, wherein —C$_1$-C$_3$ alkyl and —OC$_1$-C$_3$ alkyl are optionally substituted with 1-7 halogens.

In some embodiments of the invention, HET(2) is a bicyclic or spirocyclic heterocycle having two 3-6 membered heterocyclic rings which are fused or are connected through a single carbon atom to make a spirocyclic connection, wherein HET(2) has 2-4 heteroatoms or heteroatom groups which are O, S, S(O)$_2$, N, or NH, and optionally comprises 1-2 double bonds.

In some embodiments of the invention, Ar$^1$ and Ar$^2$ are each independently:
  (a) Phenyl optionally substituted with 1-2 groups which are independently F, Cl, Br, —CN, —CH$_3$ optionally substituted with 1-3 F, —OC$_{1-2}$ alkyl optionally substituted with 1-5 F, —OCH(CH$_3$)$_2$, —CO$_2$R$^8$, or —SO$_2$CH$_3$, wherein phenyl is optionally substituted with one group phenyl which is optionally substituted with 1-2 groups which are independently —CH$_3$, —CF$_3$, —OCH$_3$, —OCF$_3$, F, Cl or —CO$_2$R$^8$;
  (b) Phenyl optionally substituted with 1-2 groups which are independently halogen, —CH$_3$, —CF$_3$, —OCH$_3$, or —OCF$_3$, wherein phenyl is substituted with —NH-tetrahydrohydrofuryl or with a N-containing heterocycle attached through the N of the heterocycle, wherein the heterocycle is pyrrolidinyl, piperidinyl, azetidinyl, morpholino, or 2-oxa-6-azaspiro[3,3]heptane, wherein the N-containing heterocycle in all cases is optionally substituted with 1-2 groups which are F, —OH, —CH$_3$, —CF$_3$, —OCH$_3$, or —OCF$_3$;
  (c) Pyridinyl optionally substituted with one group morpholino and optionally 1-2 groups which are independently F, Cl, —CH$_3$, —CF$_3$, or —OC$_{1-3}$alkyl optionally substituted with 1-7 F; or
  (d) 2-Thiazolyl optionally substituted with one group which is —CH$_3$, —CF$_3$, —OCH$_3$, —OCF$_3$, or F.

In some embodiments of the invention, n is 0, 1, 2, 3, or 4.

In some embodiments of the invention, n is 0, 1, 2, or 3.

In some embodiments of the invention, n is 0, 1, or 2.

In some embodiments of the invention, n is 0 or 1.

In some embodiments of the invention, n is 0.

In some embodiments of the invention, each R$^1$ is independently H, halogen, —C$_1$-C$_4$ alkyl, or —OC$_1$-C$_4$ alkyl, wherein —C$_1$-C$_4$ alkyl and —OC$_1$-C$_4$ alkyl are each optionally substituted with 1-9 halogens.

In some embodiments of the invention, Each R$^1$ is independently H, halogen, —C$_1$-C$_3$ alkyl, or —OC$_1$-C$_3$ alkyl, wherein —C$_1$-C$_3$ alkyl and —OC$_1$-C$_3$ alkyl are optionally substituted with 1-7 halogens which are F or Cl.

In some embodiments of the invention, each R$^1$ is H, halogen, —CH$_3$, —CF$_3$, —OCH$_3$, or —OCF$_3$.

In some embodiments of the invention, R$^1$ is H, —CH$_3$ or F.

In some embodiments of the invention, R$^2$, R$^3$, R$^4$, R$^5$, R$^6$, and R$^7$ are each independently H, halogen, —C$_1$-C$_4$ alkyl or —OC$_1$-C$_4$ alkyl, wherein —C$_1$-C$_4$ alkyl and —OC$_1$-C$_4$ alkyl are optionally substituted with 1-9 halogens.

In some embodiments of the invention, R$^2$, R$^3$, R$^4$, R$^5$, R$^6$, and R$^7$ are each independently H, halogen, —C$_1$-C$_3$ alkyl or —OC$_1$-C$_3$ alkyl, wherein —C$_1$-C$_3$ alkyl and —OC$_1$-C$_3$ alkyl are optionally substituted with 1-7 halogens which are F or Cl.

In some embodiments of the invention, R$^2$, R$^3$, R$^4$, R$^5$, R$^6$, and R$^7$ are each independently H, halogen, —C$_1$-C$_2$ alkyl or —OC$_1$-C$_2$ alkyl, wherein —C$_1$-C$_2$ alkyl and —OC$_1$-C$_2$ alkyl are each optionally substituted with 1-5 halogens which are F.

In some embodiments of the invention, R$^2$, R$^3$, R$^4$, R$^5$, R$^6$, and R$^7$ are each H.

In some embodiments of the invention, R$^8$ is H or —C$_{1-4}$alkyl optionally substituted with 1-9 halogens.

In some embodiments of the invention, R$^8$ is H or —C$_{1-3}$alkyl optionally substituted with 1-7 halogens.

In some embodiments of the invention, R$^8$ is H or —CH$_3$.

In some embodiments of the invention, R$^9$ is H or —C$_1$-C$_4$ alkyl.

In some embodiments of the invention, R$^9$ is H or —C$_1$-C$_3$ alkyl.

In some embodiments of the invention, R$^9$ is H or —CH$_3$.

In some embodiments of the invention, R$^{10}$ is H, —C$_1$-C$_4$ alkyl, or HET(1).

In some embodiments of the invention, R$^{10}$ is H, —C$_1$-C$_3$ alkyl, or a 5-6-membered heterocycle having 1-2 heteroatoms which are each O or S, and optionally 1-3 double bonds.

In some embodiments of the invention, R$^{10}$ is H, —C$_1$-C$_2$alkyl, or a 5-6-membered heterocycle having one heteroatom which is O or S and optionally one double bond.

In some embodiments of the invention, R$^{10}$ is H, —CH$_3$ or a 5-6-membered saturated heterocycle having 1 heteroatom which is S or O.

In some embodiments of the invention, R$^{10}$ is H, —CH$_3$ or a 5-6-membered saturated heterocycle having 1 heteroatom which is O.

In some embodiments of the invention, R$^{10}$ is H, —CH$_3$ or a tetrahydrofuryl group.

Definitions and Abbreviations

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, n-butyl, sec-butyl, tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group. Alkyl groups that are shown as difunctional are alkylene groups, even if they are referred to as alkyl groups.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" when used to describe a substituent or group in a structure means a monocyclic or bicyclic compound in which the rings are aromatic and which contain only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocycle" or "heterocyclic" means a fully or partially saturated cyclic compound containing 1 or more heteroatom groups which may be one or more of N, S, O, S(O), $S(O)_2$, or (N)R, and may have one or more double bonds, where R is H or a substituent group. In general, when heterocycles are defined herein, the definition will include the number of ring members, the number of double bonds (if any), and the specific heteroatoms. The heterocycles in some cases will be aromatic, depending on the number of double bonds (e.g. 6-membered ring with 3 double bonds). Aromatic heterocycles are also referred to as heteroaromatics. S(O), $S(O)_2$, and N(R) are referred to as heteroatom groups, and each heteroatom group is counted as one ring member, as is also the case for N, S, and O.

"Benzoheterocycle" represents a phenyl ring fused to a heterocyclic ring. Examples include indole, benzofuran, 2,3-dihydrobenzofuran and quinoline.

"AcN" is acetonitrile.
"Boc" is tert-butoxycarbonyl.
"n-BuLi" is n-butyl lithium.
"Celite®" is a trade name for diatomaceous earth.
"DBU" is 1,8-diazabicyclo[5.4.0]undec-7-ene.
"D-Epoxone" is a commercial epoxidation catalyst.
"DIPEA" and "DIEA" are N,N-diisopropylethylamine.
"DCM" is dichloromethane.
"DIBAL-H" is diisobutylaluminum hydride.
"DMF" is N,N-dimethylformamide.
"DMA" is dimethylacetamide.
"DMAP" is 4-dimethylaminopyridine.
"DMSO" is dimethyl sulfoxide.
"DOPC" is 1,2-dioleoyl-sn-glycero-3-phosphocholine.
"EDTA" is ethylenediaminetetraacetic acid.

"EtOAc" is ethyl acetate.
"EtOH" is ethanol.
"Halogen" includes fluorine, chlorine, bromine and iodine.
"HPLC" is high pressure liquid chromatography.
"IPA" is isopropyl alcohol.
"LCMS" is liquid chromatography mass spectrometry.
"LiHMDS" is lithium hexamethyldisilazide.
"Me" represents methyl.
"MeCN" is acetonitrile.
"MeOH" is methanol.
"NMP" is N-methyl-2-pyrrolidone.
"OAc" is acetate.
"OXONE®" is a commercial persulfate oxidizing agent from DuPont.
"$Pd_2dba_3$" is Tris(dibenzylideneacetone)dipalladium(0), a catalyst precursor.
"PEG" is poly(ethylene glycol).
"RBF" is a round bottom flask.
"Rochelle's salt" is potassium sodium tartrate.
"RT" is an abbreviation for room temperature.
"RuPhos" is Chloro-(2-Dicyclohexylphosphino-2',6'-diisopropoxy-1,1'-biphenyl)[2-(2-aminoethyl)phenyl]palladium(II), a commercial catalyst precursor.
"SFC" is supercritical fluid chromatography.
"SM" is starting material.
"SPhos" is 2-Dicyclohexylphosphino-2',6'-dimethoxybiphenyl, a ligand.
"TEA" is triethylamine.
"TFA" is trifluoroacetic acid.
"THF" is tetrahydrofuran.
"TLC" is thin layer chromatography.
"Xantphos" is (9,9-Dimethyl-9H-xanthene-4,5-diyl)bis (diphenylphosphine), a ligand.

The term "composition," as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I and a pharmaceutically acceptable carrier.

The substituent "tetrazole" means a 2H-tetrazol-5-yl substituent group and tautomers thereof.

Optical Isomers-Diastereomers-Geometric Isomers-Tautomers

The compounds disclosed herein generally have at least two asymmetric centers, and can thus occur as pure stereoisomers and as mixtures of stereoisomers, including racemates, racemic mixtures, single enantiomers, mixtures of enantiomers, diastereomeric mixtures and individual diastereomers. Different stereoisomers having the same 2-dimensional chemical structure may have different levels of activity with respect to CETP inhibition, so that some stereoisomers may have higher activity than others. The compounds that are potent inhibitors of CETP may have utility in patients for raising HDL-C, lowering LDL-C, treating dyslipidemia, and for preventing, treating or delaying the onset of conditions that are related to atherosclerosis. Stereoisomers that have little or no activity may have utility as research tools for better understanding CETP inhibition. All stereoisomers of the claimed compounds thus have utility. The compounds of Formula I may also occur as atropisomers (rotamers) due to hindered rotation, which may be observable by NMR spectroscopy, and in some cases may be stable enough with respect to conversion by bond rotation to other atropisomers that they can be isolated and assayed.

Salts

The term "pharmaceutically acceptable salts" refers to salts prepared from pharmaceutically acceptable non-toxic bases or acids including inorganic or organic bases and inorganic or organic acids. When the compound of Formula I is acidic, salts may be derived from inorganic bases including aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, triethanolamine, trimethylamine, tripropylamine, tromethamine, and the like.

When the compound of Formula I is basic, salts may be prepared from pharmaceutically acceptable non-toxic acids, including inorganic and organic acids. Such acids include acetic, adipic, ascorbic, benzenesulfonic, benzoic, camphorsulfonic, citric, diethylacetic, ethanesulfonic, formic, fumaric, gluconic, glutamic, hydrobromic, hydrochloric, isethionic, isonicotinic, lactic, maleic, malic, malonic, mandelic, methanesulfonic, mucic, naphthalenedisulfonic, nitric, oxalic, pamoic, pantothenic, phenylpropionic, phosphoric, pimelic, pivalic, propionic, salicylic, succinic, sulfuric, sulfaminic, tartaric, p-toluenesulfonic acid, trifluoroacetic and the like. Particularly preferred are citric, hydrobromic, hydrochloric, maleic, phosphoric, sulfuric, and tartaric acids.

It will be understood that, as used herein, references to the compounds of Formula I and to the examples are meant to also include the pharmaceutically acceptable salts and prodrugs, where such salts and prodrugs are possible.

Prodrugs

Prodrugs, which are compounds that are converted to the compound of Formula I as they are being administered to a patient or after they have been administered to a patient, are also compounds of formula I in the sense that they provide the claimed pharmaceutically active drug moiety to the patient.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

The compounds disclosed herein, including pharmaceutically acceptable salts thereof, are potent inhibitors of CETP. The compounds may therefore be useful in treating mammalian patients, preferably human patients, having diseases and conditions that are treated by inhibition of CETP.

One aspect of the present invention provides a method for treating or reducing the risk of developing a disease or condition that may be treated or prevented by inhibition of CETP by administering a therapeutically effective amount of the compound of Formula I to a patient in need of treatment. The patient is a human or mammal, but is most often a human. A "therapeutically effective amount" is the amount of compound that is effective in obtaining a desired clinical outcome in the treatment of a specific disease or condition.

Diseases or conditions that may be treated with the compounds of Formula I, or which the patient may have a reduced risk of developing as a result of being treated with the compounds of Formula I, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome. There are reports in the scientific literature that suggest that inhibition of CETP may have utility in preventing or slowing the development of Alzheimer's disease. The compounds of Formula I may therefore have utility in preventing or delaying the progression of Alzheimer's disease or other neurodegenerative diseases.

The compounds disclosed herein are particularly effective in raising HDL-C and/or increasing the ratio of HDL-C to LDL-C. The compounds may also be effective in reducing LDL-C, and may be effective in treating dyslipidemia. These changes in HDL-C and LDL-C may be beneficial in treating atherosclerosis, reducing or delaying the development of atherosclerosis, reducing the risk of developing atherosclerosis, or preventing atherosclerosis. The compounds disclosed herein may thus be beneficial in treating atherosclerosis, reducing or delaying the development of atherosclerosis, reducing the risk of developing atherosclerosis, or preventing atherosclerosis.

Likely indications for atherosclerosis and dyslipidemia using the compounds described herein are written below, where the drug product is titled "CETP inhibitor:"

Atherosclerosis. In patients at high risk of cardiovascular events because of existing coronary, cerebrovascular, or peripheral vascular disease, CETP inhibitor co-administered with an HMG-CoA reductase inhibitor is indicated to reduce the risk of coronary mortality, myocardial infarction, coronary revascularization procedures, ischemic stroke, and cardiovascular death.

Dyslipidemia. CETP inhibitor co-administered with a statin is indicated to reduce elevated LDL-C, apolipoprotein B (ApoB), lipoprotein a (Lp(a)), non-HDL-C, and total cholesterol; and increase HDL-C and apolipoprotein A-1 (Apo A-1) in patients with mixed or primary dyslipidemia.

Administration and Dose Ranges

Any suitable route of administration may be employed for providing a mammal, especially a human, with an effective dose of the compounds described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the compound of Formula I is administered orally.

When treating the diseases for which the compound of Formula I is indicated, generally satisfactory results are expected when the compound of Formula I is administered at a daily dosage of from about 0.1 milligram to about 1000 milligram in one dose daily or divided into more than one dose per day.

Oral administration will usually be carried out using tablets. Examples of doses in tablets include 0.1 mg, 0.5 mg, 1 mg, 2 mg, 5 mg, 10 mg, 25 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 275 mg, 300 mg, 350 mg, 400 mg, 450 mg, 500 mg, and 1000 mg. Other oral forms can also have the same dosages (e.g. capsules). A preferred dose is likely in the range of 50-200 mg.

Pharmaceutical Compositions

Another aspect of the present invention provides pharmaceutical compositions which comprise the compound of Formula I and a pharmaceutically acceptable carrier. The pharmaceutical compositions of the present invention comprise the compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. A pharmaceutical composition may also consist essentially of the compound of Formula I, or a pharmaceutically acceptable salt of the compound, and a pharmaceutically acceptable carrier, without other therapeutic ingredients.

Pharmaceutical compositions may be formulated to be suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compound can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compound of formula I may also be administered parenterally. Solutions or suspensions of the compound can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compound of Formula I, including pharmaceutically acceptable salts thereof, may be used in pharmaceutical combinations with other drugs that may also be useful in the treatment or amelioration of the diseases or conditions for which the compound of Formula I is useful. Such other drugs may be administered, by a route and in an amount commonly used therefor, contemporaneously or sequentially with the compound of Formula I. When the compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered concomitantly, on the same or different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of formula I and the other active ingredients may be used in lower doses than when each is used singly. Accordingly, the pharmaceutical compositions of the compound of formula I include those that contain one or more other active ingredients, in addition to the compound of Formula I.

The compound of Formula I will likely be approved initially for coadministration with a statin, which could be administered in the form of a fixed dose combination of the compound of formula I and a statin. Additional drugs may also be administered in combination with the compound of Formula I and the statin, either by coadministration or in a fixed dose combination. The compound of formula I and the drugs that are administered with it may be administered as pharmaceutically acceptable salts, as prodrugs, or otherwise formulated for immediate release, extended release, or controlled release, as necessary.

Examples of statins that may be administered in combination with the compound of Formula I include, but are not limited to, (i) simvastatin and lovastatin which are marketed as ZOCOR® and MEVACOR® in lactone prodrug form and function as inhibitors after administration, and (ii) dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), and pitavastatin (particularly the calcium salt sold in LIVALO®), and (iii) other statins that may yet be developed. Preferred statins for combination therapy include atorvastatin, rosuvastatin, and simvasatin, as described above.

Cholesterol absorption inhibitors, and particularly ezetimibe (ZETIA®), as well as other cholesterol absorption inhibitors, such as stanol esters, beta-sitosterol, sterol glycosides such as tiqueside, and other azetidinones, may be administered with the compound of Formula I, generally with a statin, as described above. The preferred cholesterol absorption inhibitor is ezetimibe. Combinations of the compound of formula I with a statin and a cholesterol inhibitor, such as ezetimibe, are also contemplated. Preferred 3-component combinations include combinations of the compound of formula I with simvastatin, atorvastatin, or rosuvastatin in combination with ezetimibe, where the statins may be salt forms or prodrugs as described above. The combination of simvastatin with ezetimibe is currently marketed as VYTORIN®.

Other cholesterol reducing drugs that may be coadministered with the compound of formula I in addition to HMG-CoA reductase inhibitors (statins) and cholesterol absorption inhibitors include (i) bile acid sequestrants, as for example cholestyramine, colestipol, dialkylaminoalkyl derivatives of a cross-linked dextran, Colestid®, and LoCholest®, (ii) niacin and related compounds, such as nicotinyl alcohol, nicotinamide, and nicotinic acid or a salt thereof, in an immediate release or extended release form, which may optionally be in the form of a combination with a DP-1 antagonist, such as laropiprant, (iii) PPARα agonists, such as gemfibrozil and fenofibric acid derivatives (fibrates), including clofibrate, fenofibrate, bezafibrate, ciprofibrate, and etofibrate, (iv) acyl CoA:cholesterol acyltransferase (ACAT) inhibitors, such as avasimibe and melinamide, and including selective ACAT-1 and ACAT-2 inhibitors and dual inhibitors, (v) phenolic anti-oxidants, such as probucol, (vi) microsomal triglyceride transfer protein (MTP)/ApoB secretion inhibitors, (vii) anti-oxidant vitamins, such as vitamins C and E and beta carotene, (viii) thyromimetics, (ix) LDL (low density lipoprotein) receptor inducers, (x) platelet aggregation inhibitors, for example glycoprotein IIb/IIIa fibrinogen receptor antagonists and aspirin, (xi) vitamin B12 (also known as cyanocobalamin), (xii) folic acid or a pharmaceutically acceptable salt or ester thereof, such as the sodium salt and the methylglucamine salt, (xiii) FXR and LXR ligands, including both inhibitors and agonists, (xiv) agents that enhance ABCA1 gene expression, (xv) ileal bile acid transporters, and (xvi) niacin receptor agonists (e.g. acipimox and acifran) and partial agonists.

Finally the compound of formula I can be combined with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these diseases, allowing for the possibility of administering reduced doses of active ingredients, such as doses that otherwise might be sub-therapeutic.

Examples of other active ingredients that may be administered in combination with a compound of formula I include, but are not limited to, compounds that are primarily antidiabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, LY-818, and compounds described in WO 02/060388, WO 02/08188, WO 2004/019869, WO 2004/020409, WO 2004/020408, and WO2004/066963);

(b) biguanides such as metformin, phenformin, and pharmaceutically acceptable salts thereof, in particular metformin hydrochloride and extended release formulations thereof, such as Glumetza™, Fortamet™, and GlucophageXR™;

(c) protein tyrosine phosphatase-1B (PTP-1B) inhibitors, such as ISIS-113715 and TTP814;

(d) dipeptidyl peptidase IV (DP-IV) inhibitors, including sitagliptin, vildagliptin, saxagliptin, alogliptin, linagliptin, dutogliptin, teneligliptin, MK-3102, and gemigliptin;

(e) insulin or insulin mimetics, such as for example insulin lispro, insulin glargine, insulin detemir, insulin glulisine, insulin degludec, SBS1000, insulin zinc suspension, and oral and inhalable formulations of insulin and insulin analogs;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 mimetics, GLP-1 analogs, and GLP-1 receptor agonists, such as exendins, e.g. exenatide (BYETTA), dulaglutide, semaglutide, albiglutide, liraglutide, lixisenatide, and taspoglutide, including intranasal, tranxsdermal, and once weekly formulations thereof, and oxyntomodulin analogs and derivatives, and non-peptidyl GLP-1 receptor agonists;

(l) GIP-1;

(m) amylin and amylin analogs (e.g. pramlintide);

(n) Non-sulfonylurea insulin secretagogues, such as the meglitinides (e.g. glimepiride, mitiglinide, meglitinide, nateglinide, and rapeglinide); and (o) leptin and leptin derivatives and agonists.

Preferred combinations with antidiabetic compounds include combinations of the compounds disclosed herein with DP-IV inhibitors (sitagliptin, vildagliptin, saxagliptin, alogliptin, linagliptin, dutogliptin, teneligliptin, omarigliptin, and gemigliptin), combinations with biguanides, and combinations with both a DP-IV inhibitor and a biguanide. The preferred DP-IV inhibitor is sitagliptin, and the preferred biguanide is metformin in the formulations and salt forms described above.

Other active ingredients that may be used in combination with the compound of formula I include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and $\beta_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compound of formula I. Examples of antihypertensive compounds that may be used with the compound of formula I include thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerancne, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104, 869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063, 208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885, 292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S), 5(S),7(S)—N-(2-carbamoyl-2-methylpropyl)-5-amino-4-hydroxy-2,7-diisopropyl-8-[4-methoxy-3-(3-methoxy-propoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); and nitrates or nitric oxide donating compounds, e.g. isosorbide mononitrate.

Preferred antihypertensives that may be used in combination with the CETP inhibitors disclosed herein include one or more of an angiotensin II antagonist (losartan), an ACE inhibitor (enalapril or captopril), and hydrochlorothiazide.

Anti-obesity compounds may be administered in combination with the compounds of Formula I, including: (1) growth hormone secretagogues and growth hormone secretagogue receptor agonists/antagonists, such as NN703 and hexarelin; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14] Bn(6-14) and [D-Phe6,Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) $ACC_2$ (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of Formula I may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

Assays

Protocol: Scintillation Proximity Assay (SPA) for CETP Activity

First, low density lipoprotein (LDL) (Meridian) was biotinylated by incubating LDL with biotin for 1 hour on ice, after which it was dialyzed to remove free biotin. Then compounds at varying concentrations were incubated with 15 nM CETP (reagent production group, In Vitro Pharmacology, MRL Rahway) and 50 ug/ml of the biotinylated LDL in 50 mM HEPES, 150 mM NaCl, pH 7.4, for 1 hour at 37° C. The reaction was started by adding $^3$H-cholesterol ester high density lipoprotein (HDL) (American Radiochemicals Corp) at a concentration of ~0.6 nM. The reaction proceeded for 2 hours at 37° C., after which time it was quenched by the addition of 12% acetic acid. PVT streptavidin-coated scintillation proximity beads, which had been brought to room temperature, were then added at a concentration of 4 mg/ml. The assay was then mixed and counted after one half hour in a Microbeta plate reader.

In Vitro Radioactive Assays of CETP-Catalyzed CE and TG Transfer (RTA Assay)

Reagents and sources are: [3H] cholesteryl oleate (GE #TRK.886), [3H] Triolein (Perkin-Elmer NET-431), Butylated hydroxyl toluene (Aldrich, #D4740-4), DOPC (Sigma, #P6354), Sodium Bromide (Fisher scientific #S255-500), PEG 8000 (Fisher, #BP233-1), and human HDL (Intracel Corp #RP-036).

An in vitro assay for determining $IC_{50}$'s to identify compounds that inhibit CETP transfer activity is performed based on a modification of a published method (Morton and Zilversmit, (1981) A plasma inhibitor of triglyceride and cholesteryl ester transfer activities, J. Biol. Chem. 256(23), 11992-11995). The ability of inhibitors to alter CETP activity is performed using two different assays: one using recombinant CETP and one using an endogenous plasma source of CETP. Both assays measure the transfer of [3H] cholesteryl oleate or [3H] triolein from exogenous LDL to HDL.

Radiolabeled donor particles are generated by first combining 100 μl of 200 μM butylated hydroxyl toluene in $CHCl_3$, 216 μL of 21.57 mM DOPC in EtOH, and either 500 μCi [3H]-triolein (Perkin Elmer #NET-431) or 500 μCi [3H]-cholesteryl oleate (GE #TRK886) in a glass tube. Reagents are mixed, dried under nitrogen, and then resuspended in 2 mL of 50 mM Tris, 27 μM EDTA at pH 7.4. After a brief vortex, the solution is sonicated until clear and mixed with 20 mL of fresh human serum. The mixture is incubated overnight at 37° C. The [3H] labeled LDL substrate is separated at 1.063 g/ml density by sequential ultracentrifugal flotation in NaBr according to the method of Havel, Eder, et al., 1955, and Chapman, Goldstein, et al., 1981. Once isolated the particles are dialyzed 3× in CETP buffer (50 mM Tris, pH 7.4, 100 mM NaCl, 1 mM EDTA). Human HDL is purchased from Intracel and used as the acceptor particles.

Transfer assays are performed in a 96-well v-bottom polypropylene plate. For the RTA using recombinant CETP (2% RTA), an assay cocktail is prepared with the final concentrations 128 μg/mL HDL, 20 nM rCETP, 2% human serum, and 1×CETP buffer. 1 μL of each test compound diluted in DMSO is added to 47 μL of assay cocktail per well and incubated at 37° C. for 1 hour. To initiate the transfer reaction, 2 μL radiolabeled LDL is added. After an additional 60 min of incubation at 37° C., the transfer action is terminated by precipitation of LDL with an equal volume of 20% W/V PEG 8000. The plates are centrifuged at 2000 rpm for 30 minutes at 4° C. A 40 μL aliquot of the HDL-containing supernatant is transferred to a Packard Opti-plate™ with 200 μL of MicroScint™ 20. After mixing, plates are counted by liquid scintillation. Counts present in the supernatant for blanks (wells containing only HDL acceptor, CETP buffer and DMSO) are subtracted from those containing test compounds and used to correct for non-specific transfer.

For the transfer assay using endogenous CETP from serum (95% RTA), the same procedure is used except that human serum is added such that a final concentration of serum of 95% of the total assay volume is achieved, yielding a concentration of approximately 15 nM endogenous CETP in the assay. This is then combined with HDL and CETP buffer and the reaction proceeds as above and is terminated as described.

Comparison of the counts of samples with inhibitors to an uninhibited (DMSO only) positive control yield a percent inhibition. A plot of percent inhibition vs. log of inhibitor concentration, fit to a Sigmoidal 4 parameter equation is used to calculate IC50.

EXAMPLES

The following schemes and examples are provided so that the invention will be more fully appreciated and understood. These examples are illustrative and are not to be construed as limiting the invention in any way. The claims appended hereto define the scope of the invention.

The examples were synthesized according to the general schemes shown below. Synthetic intermediates for making the compounds were made as described below and as illustrated in the following schemes. The various starting materials are commercially available or are readily made by persons skilled in the art. All examples were synthesized and were assayed for CETP inhibition activity using the RTA assays in 2% and/or 95% human serum. All of the examples had IC50's between 25 and 9683 nM using one or both of the RTA assays described above and are therefore CETP inhibitors. Preferred compounds have IC50's less than about 500 nM.

General Synthetic Schemes

Scheme A1

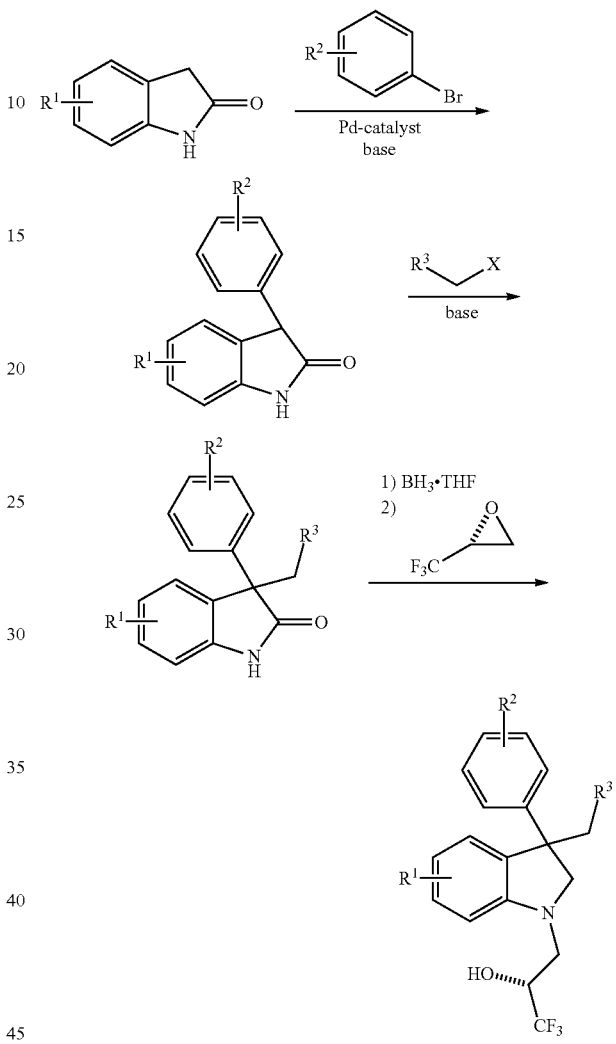

Scheme A2

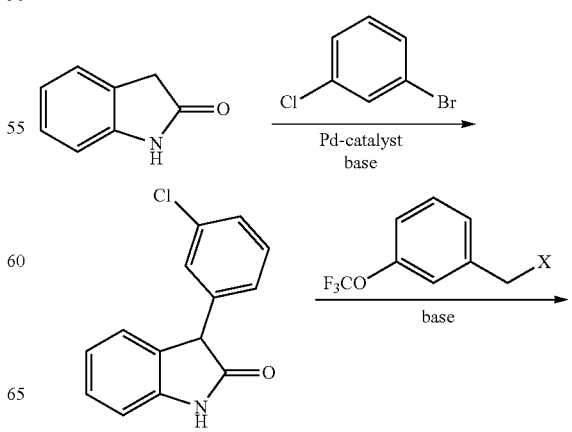

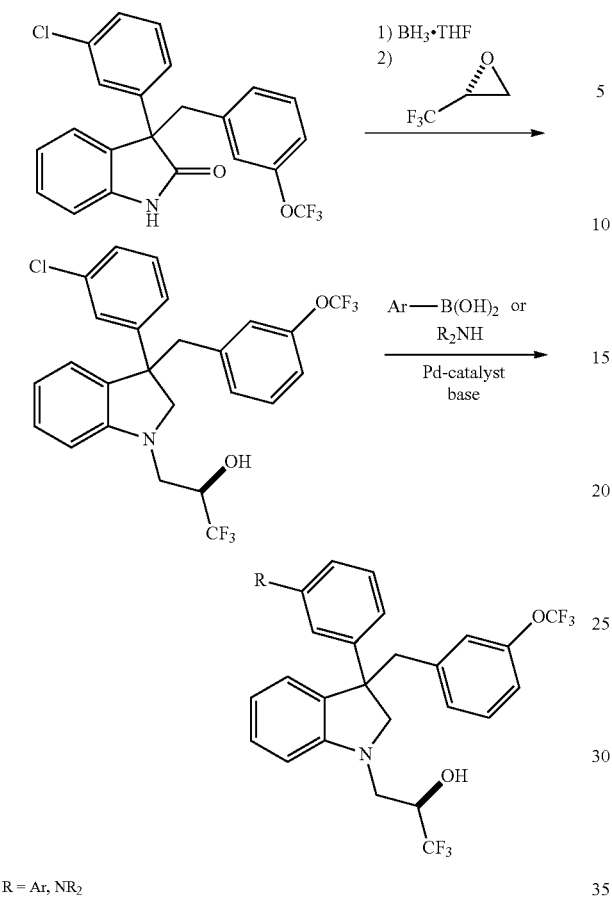
R = Ar, NR₂
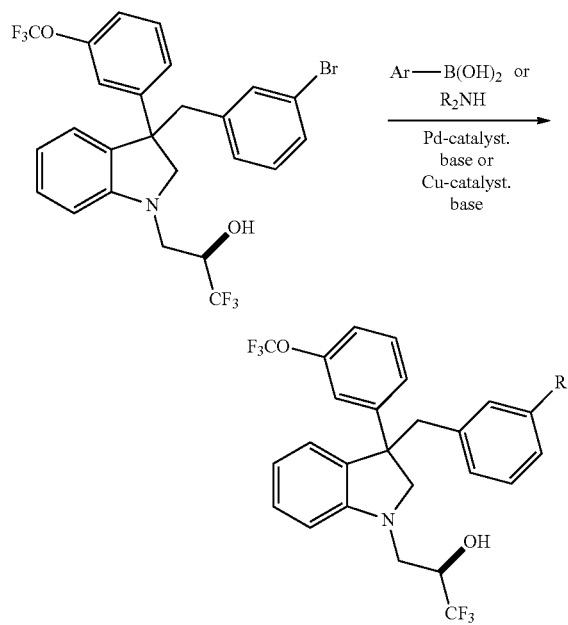
R = Ar, NR₂, CO₂R, CN, SO₂Me
Syntheses of Examples
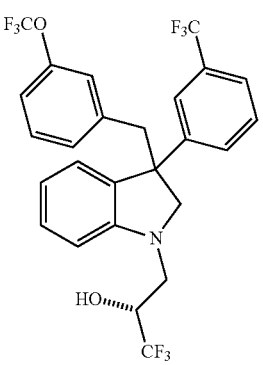 [SMILES: O[C@H](CN1CC(Cc2cccc(OC(F)(F)F)c2)(c2cccc(C(F)(F)F)c2)c2ccccc21)C(F)(F)F]
Example 1
(2R)-1,1,1-trifluoro-3-(3-(3-(trifluoromethoxy)benzyl)-3-(3-(trifluoromethyl)-phenyl)indolin-1-yl)propan-2-ol. This material was prepared according to Scheme A1, as described below.
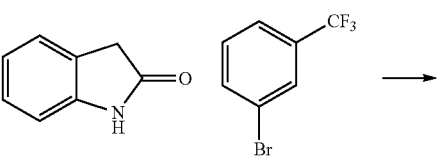
Scheme A3
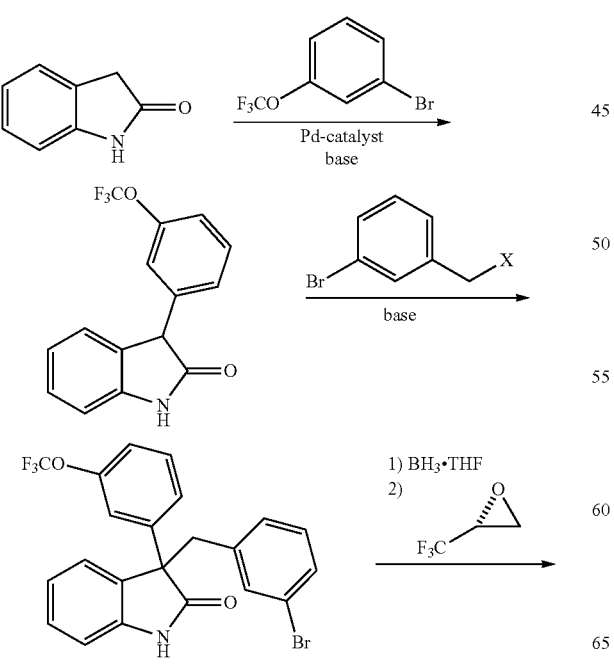

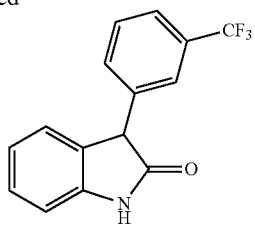

3-(3-(trifluoromethyl)phenyl)indolin-2-one. Oxindole (1.598 g, 12 mmol), 3-bromo-α,α,α-trifluoromethyltoluene (2.009 ml, 14.40 mmol), potassium carbonate (3.32 g, 24.00 mmol), Pd$_2$dba$_3$ (0.220 g, 0.240 mmol), and 2-(dicyclohexylphosphino)-2',4',6'-triisopropylbiphenyl (0.458 g, 0.960 mmol) were combined in THF (12 ml) and the mixture was degassed with nitrogen. The solution was then heated to 80° C. for 18 h. The mixture was cooled to room temperature, filtered through silica eluting with ethyl acetate, and concentrated. The material was then purified by silica gel chromatography (Biotage 100 g SNAP cartridge, 0-50% ethyl acetate in hexanes) to provide 3-(3-(trifluoromethyl)phenyl)indolin-2-one as a white solid.

$^1$H NMR (500 MHz) δ 8.58 (s, 1H), 7.61 (d, J=7 Hz, 1H), 7.53-7.45 (m, 3H), 7.33-7.29 (m, 1H), 7.16 (d, J=7 Hz, 1H), 7.10 (m, 1H), 7.01-6.90 (m, 1H), 4.73 (s, 1H).

LCMS m/z=278.0 (M+H)

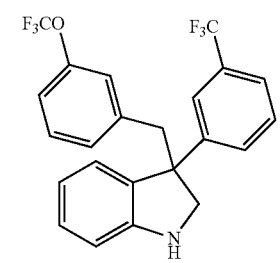

3-(3-(trifluoromethoxy)benzyl)-3-(3-(trifluoromethyl)phenyl)indolin-2-one. 3-Trifluoromethoxy-benzylbromide (0.204 ml, 1.255 mmol) was added to a mixture of 3-(3-(trifluoromethyl)-phenyl)indolin-2-one (290 mg, 1.046 mmol) and potassium carbonate (289 mg, 2.092 mmol) (sodium carbonate may be used in place of potassium carbonate) in DMA (2.5 ml). The mixture was stirred at r.t. for 16 h. The reaction was diluted with ethyl acetate and washed with water (3×5 mL). The organic layer was dried with Na$_2$SO$_4$, filtered, and concentrated. The products were then purified by silica gel chromatography (Biotage 50 g SNAP cartridge; 0-40% ethyl acetate in hexanes) to provide 3-(3-(trifluoromethoxy)benzyl)-3-(3-(trifluoromethyl)-phenyl)indolin-2-one.

$^1$H NMR (500 MHz) δ 7.79 (s, 1H), 7.73 (d, J=7 Hz, 1H), 7.62-7.60 (m, 2H), 7.51 (t, J=7 Hz, 1H), 7.26-7.22 (m, 2H), 7.14 (t, J=7.0 Hz, 1H), 7.11 (m, 1H), 6.97 (m, 1H), 6.92 (m, 1H), 6.78 (m, 1H), 6.73 (s, 1H), 3.77 (d, J=13 Hz, 1H), 3.49 (d, J=13 Hz, 1H)

LCMS m/z=451.8 (M+H).

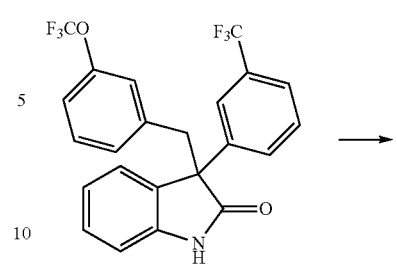

3-(3-(trifluoromethoxy)benzyl)-3-(3-(trifluoromethyl)phenyl)indoline. Borane tetrahydrofuran complex (1.673 ml, 1.673 mmol) was added to a solution of 3-(3-(trifluoromethoxy)benzyl)-3-(3-(trifluoromethyl)phenyl)indolin-2-one (302 mg, 0.669 mmol) in THF (1.5 ml). The mixture was heated to 70° C. for 20 h. The reaction was cooled to room temperature and quenched with saturated NH$_4$Cl solution, and this mixture was stirred vigorously for 20 minutes. The product was extracted with ethyl acetate. The extracts were dried over Na$_2$SO$_4$, filtered, and concentrated. The product was purified by silica gel chromatography (Biotage 25 g SNAP cartridge, 0-50% ethyl acetate in hexanes) to provide 3-(3-(trifluoromethoxy)benzyl)-3-(3-(trifluoromethyl)phenyl)indoline. This material may also be used without purification in the final step of the sequence, epoxide opening.

$^1$H NMR (500 MHz) δ 7.66 (s, 1H), 7.59 (d, J=7 Hz, 1H), 7.53 (d, J=7 Hz, 1H), 7.45 (t, J=8 Hz, 1H), 7.18-7.13 (m, 2H), 7.04 (d, J=8 Hz, 1H), 6.98 (d, J=7 Hz, 1H), 6.81 (t, J=7.5 Hz, 1H), 6.71 (m, 2H), 6.60 (s, 1H), 3.83 (m, 1H), 3.75-3.73 (m, 2H), 3.46 (d, J=13 Hz, 1H), 3.41 (d, J=13 Hz, 1H).

LCMS m/z=437.9 (M+H)

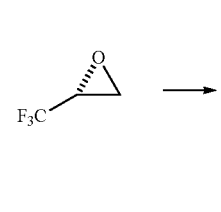

-continued

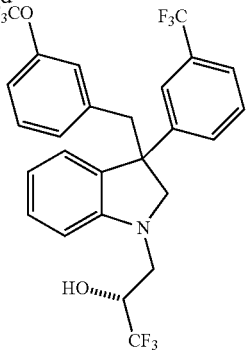

(2R)-1,1,1-trifluoro-3-(3-(3-(trifluoromethoxy)benzyl)-3-(3-(trifluoromethyl)-phenyl)indolin-1-yl)propan-2-ol. (S)-2-(trifluoromethyl)oxirane (81 μl, 0.933 mmol) was added to a solution of 3-(3-(trifluoromethoxy)benzyl)-3-(3-(trifluoromethyl)phenyl)indoline (136 mg, 0.311 mmol) in 1,1,1,3,3,3-hexafluoro-2-propanol (412 μl, 3.91 mmol). The reaction was stirred at room temperature overnight. The solvent was removed and the product was purified by silica gel chromatography (Biotage 25 g SNAP cartridge; 0-25% ethyl acetate in hexanes) to provide (2R)-1,1,1-trifluoro-3-(3-(3-(trifluoromethoxy)benzyl)-3-(3-(trifluoromethyl)phenyl)indolin-1-yl)propan-2-ol.

$^1$H NMR (500 MHz) (mixture of diastereomers) δ 7.72 (s, 0.5 H), 7.69 (s, 0.5 H), 7.65 (d, J=6.5 Hz, 0.5 H), 7.61 (d, J=7.5 Hz, 0.5 H), 7.56 (s, 1H), 7.50 (m, 1H), 7.25-7.17 (m, 2H), 7.07 (broad s, 2H), 6.91-6.89 (m, 1H), 6.79-6.75 (m, 1H), 6.53 (m, 2H), 4.00 (broad s, 1H), 3.83 (d, J=9 Hz, 0.5H), 3.77 (d, J=9 Hz, 0.5H), 3.59-3.55 (m, 1H), 3.45-3.43 (m, 1H), 3.39-3.29 (m, 2H), 3.21-3.15 (m, 1H), 2.32 (m, 0.5H), 2.15 (m, 0.5H).

LCMS m/z=549.8 (M+H)

Examples 1-25, in the table below, were prepared according to Scheme A1 in a fashion similar to that described for Example 1.

| Example no. | Structure | IC$_{50}$ RTA 2% serum (nM) | IC$_{50}$ RTA 95% serum (nM) | LCMS (M + H) |
|---|---|---|---|---|
| Example 1 | 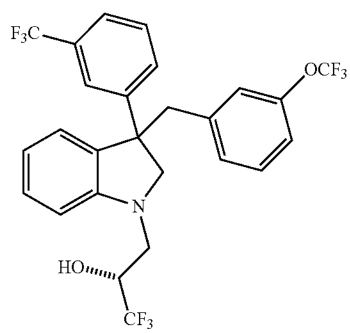 [SMILES: O[C@H](CN1CC(Cc2cccc(OC(F)(F)F)c2)(c2cccc(C(F)(F)F)c2)c2ccccc21)C(F)(F)F] | 28 | 1218 | 549.8 |
| Example 2 | 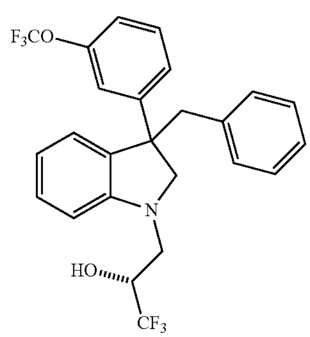 [SMILES: O[C@H](CN1CC(Cc2ccccc2)(c2cccc(OC(F)(F)F)c2)c2ccccc21)C(F)(F)F] | 238 | 746 | 482.4 |
| Example 3 | 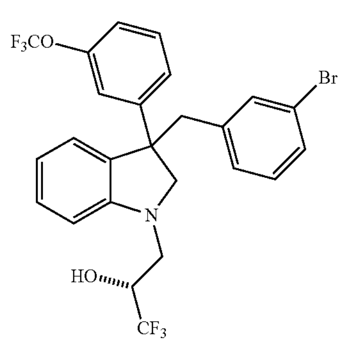 [SMILES: O[C@H](CN1CC(Cc2cccc(Br)c2)(c2cccc(OC(F)(F)F)c2)c2ccccc21)C(F)(F)F] | 67 | 308 | 562.3 |

| Example no. | Structure | IC$_{50}$ RTA 2% serum (nM) | IC$_{50}$ RTA 95% serum (nM) | LCMS (M + H) |
|---|---|---|---|---|
| Example 4 | 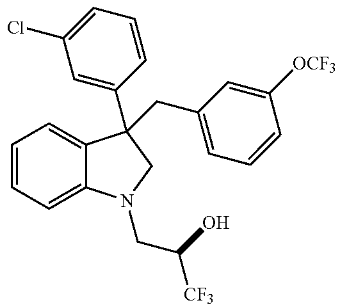 [SMILES: O[C@H](CN1CC(Cc2cccc(OC(F)(F)F)c2)(c2cccc(Cl)c2)c2ccccc21)C(F)(F)F] | 466 | 1375 | 516.3 |
| Example 5 | 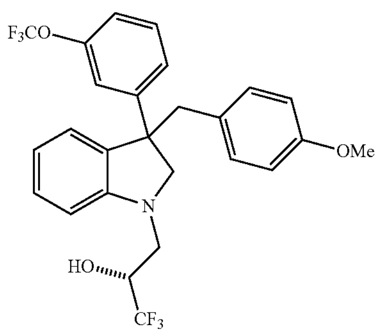 [SMILES: COc1ccc(CC2(c3cccc(OC(F)(F)F)c3)CN(C[C@@H](O)C(F)(F)F)c3ccccc32)cc1] | 2155 | 9683 | 512.3 |
| Example 6 | 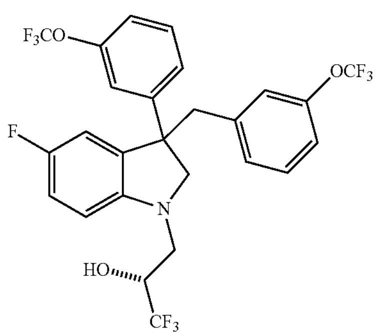 [SMILES: O[C@H](CN1CC(Cc2cccc(OC(F)(F)F)c2)(c2cccc(OC(F)(F)F)c2)c2cc(F)ccc21)C(F)(F)F] | | 763 | 584.4 |
| Example 7 | 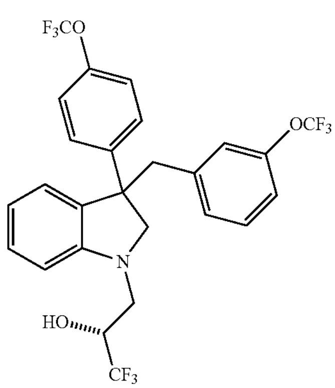 [SMILES: O[C@H](CN1CC(Cc2cccc(OC(F)(F)F)c2)(c2ccc(OC(F)(F)F)cc2)c2ccccc21)C(F)(F)F] | | 232 | 566.3 |

-continued

| Example no. | Structure | IC$_{50}$ RTA 2% serum (nM) | IC$_{50}$ RTA 95% serum (nM) | LCMS (M + H) |
|---|---|---|---|---|
| Example 8 | (structure) | 25 | 94 | 598.3 |
| Example 9 | (structure) | 1213 | 3374 | 566.3 |
| Example 10 | (structure) |  | 69 | 566.4 |
| Example 11 | (structure) | 155 | 491 | 580.5 |

-continued

| Example no. | Structure | IC$_{50}$ RTA 2% serum (nM) | IC$_{50}$ RTA 95% serum (nM) | LCMS (M + H) |
|---|---|---|---|---|
| Example 12 | 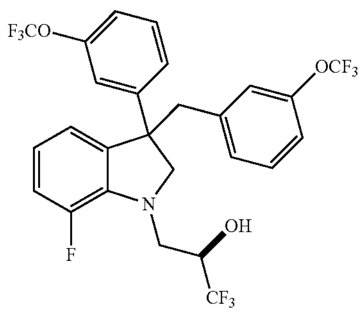 [SMILES: O[C@H](CN1CC(Cc2cccc(OC(F)(F)F)c2)(c2cccc(OC(F)(F)F)c2)c2cccc(F)c21)C(F)(F)F] | 67 | 222 | 584.2 |
| Example 13 | 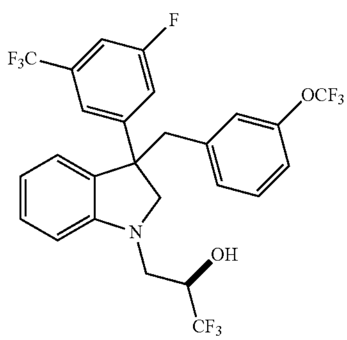 [SMILES: O[C@H](CN1CC(Cc2cccc(OC(F)(F)F)c2)(c2cc(F)cc(C(F)(F)F)c2)c2ccccc21)C(F)(F)F] | 102 | 2512 | 567.8 |
| Example 14 | 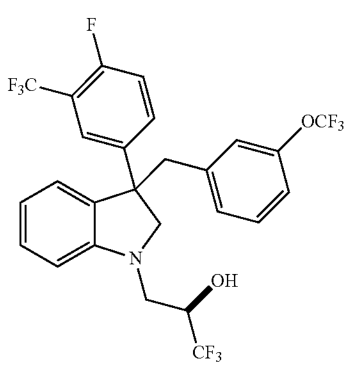 [SMILES: O[C@H](CN1CC(Cc2cccc(OC(F)(F)F)c2)(c2ccc(F)c(C(F)(F)F)c2)c2ccccc21)C(F)(F)F] | 277 | 685 | 567.9 |
| Example 15 | 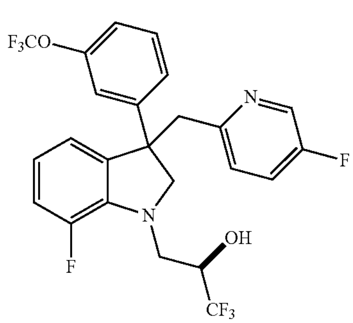 [SMILES: O[C@H](CN1CC(Cc2ccc(F)cn2)(c2cccc(OC(F)(F)F)c2)c2cccc(F)c21)C(F)(F)F] | 2855 | | 520.1 |

-continued

| Example no. | Structure | IC$_{50}$ RTA 2% serum (nM) | IC$_{50}$ RTA 95% serum (nM) | LCMS (M + H) |
|---|---|---|---|---|
| Example 16 | 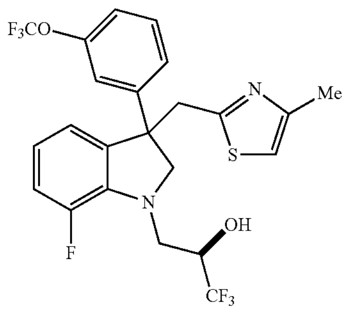 [SMILES: Cc1csc(CC2(c3cccc(OC(F)(F)F)c3)CN(C[C@@H](O)C(F)(F)F)c3c(F)cccc32)n1] | 296 | 1996 | 521.5 |
| Example 17 | 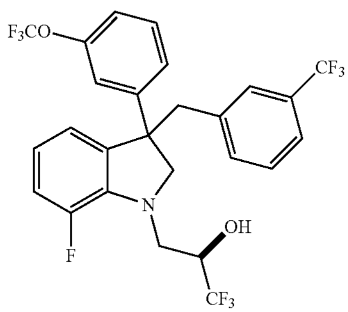 [SMILES: O[C@H](CN1CC(Cc2cccc(C(F)(F)F)c2)(c2cccc(OC(F)(F)F)c2)c2cccc(F)c21)C(F)(F)F] | 66 | 706 | 568.4 |
| Example 18 | 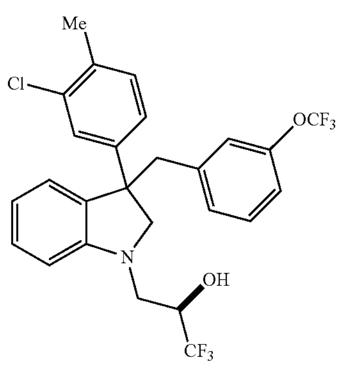 [SMILES: Cc1ccc(C2(Cc3cccc(OC(F)(F)F)c3)CN(C[C@@H](O)C(F)(F)F)c3ccccc32)cc1Cl] | 161 | 1351 | 530.0 |
| Example 19 | 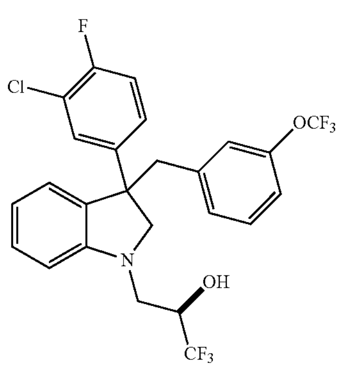 [SMILES: O[C@H](CN1CC(Cc2cccc(OC(F)(F)F)c2)(c2ccc(F)c(Cl)c2)c2ccccc21)C(F)(F)F] | 883 | 3740 | 534.0 |

-continued
| Example no. | Structure | IC$_{50}$ RTA 2% serum (nM) | IC$_{50}$ RTA 95% serum (nM) | LCMS (M + H) |
|---|---|---|---|---|
| Example 20 | 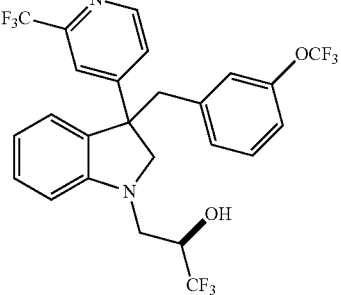 | 447 | 2602 | 550.8 |
| Example 21 | 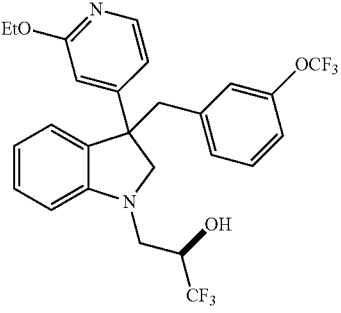 [SMILES: CCOc1cc(C2(Cc3cccc(OC(F)(F)F)c3)CN(C[C@@H](O)C(F)(F)F)c3ccccc32)ccn1] | 60 | 283 | 526.8 |
| Example 22 | 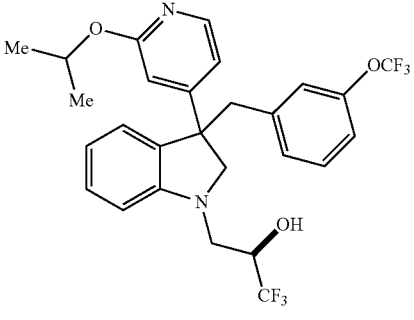 [SMILES: CC(C)Oc1cc(C2(Cc3cccc(OC(F)(F)F)c3)CN(C[C@@H](O)C(F)(F)F)c3ccccc32)ccn1] | 43 | 101 | 540.9 |
| Example 23 | 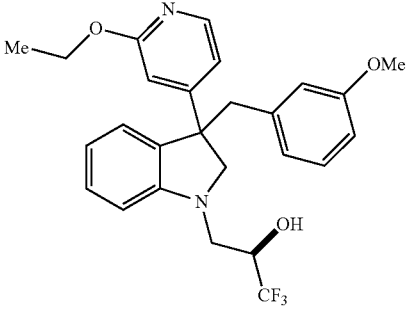 [SMILES: CCOc1cc(C2(Cc3cccc(OC)c3)CN(C[C@@H](O)C(F)(F)F)c3ccccc32)ccn1] | 249 | 681 | 472.9 |

| Example no. | Structure | IC$_{50}$ RTA 2% serum (nM) | IC$_{50}$ RTA 95% serum (nM) | LCMS (M + H) |
|---|---|---|---|---|
| Example 24 | 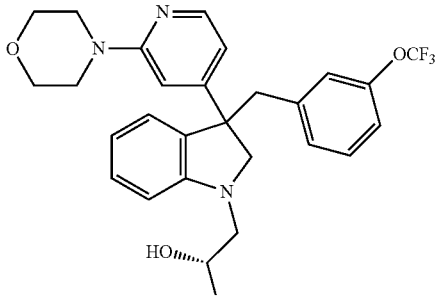 | 244 | 3123 | 568 |

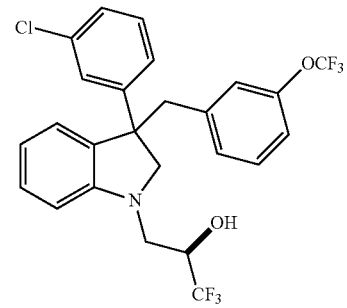 [SMILES: O[C@H](CN1CC(Cc2cccc(OC(F)(F)F)c2)(c2cccc(Cl)c2)c2ccccc21)C(F)(F)F]

Example 4

(2R)-3-(3-(3-chlorophenyl)-3-(3-(trifluoromethoxy)benzyl)indolin-1-yl)-1,1,1-trifluoropropan-2-ol. The synthesis of the intermediate (Example 4), or derivatives thereof, is used in the preparation of Examples 25-44 according to Scheme A2 and is found below.

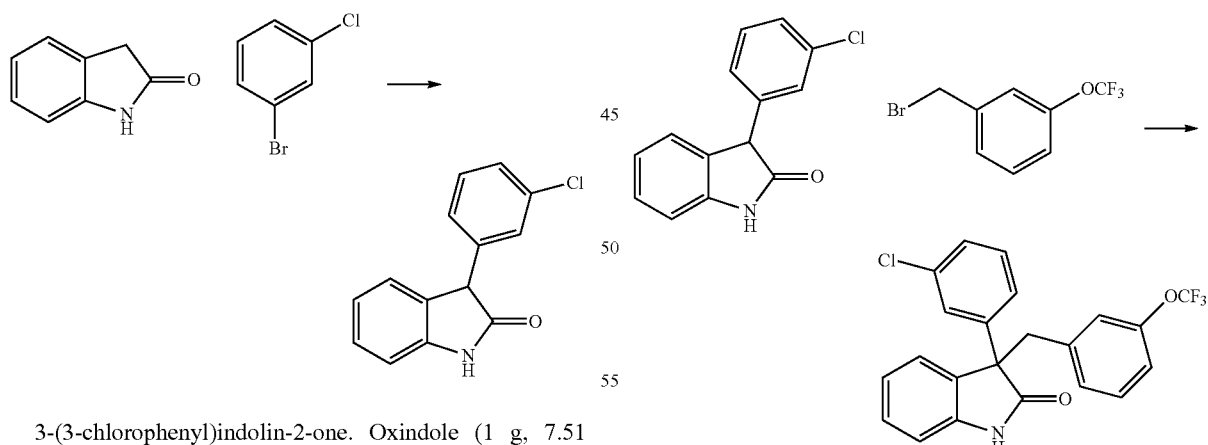

3-(3-chlorophenyl)indolin-2-one. Oxindole (1 g, 7.51 mmol), 1-bromo-3-chlorobenzene (1.059 ml, 9.01 mmol), potassium carbonate (2.076 g, 15.02 mmol), Pd$_2$dba$_3$ (0.138 g, 0.150 mmol), and 2-(dicyclohexylphosphino)-2',4',6'-triisopropylbiphenyl (0.286 g, 0.601 mmol) were combined in THF (8 ml) and the solution was degassed by bubbling nitrogen through the mixture for 5 minutes. The reaction was then heated to 80° C. for 20 h. The mixture was cooled to room temperature, diluted with ethyl acetate, and filtered through a pad of silica gel eluting with ethyl acetate. The eluent was concentrated and the crude material was purified by silica gel chromatography (Biotage 100 g SNAP cartridge, 0-40% ethyl acetate in hexanes) to provide 3-(3-chlorophenyl)indolin-2-one.

$^1$H NMR (500 MHz) δ 8.70-8.26 (broad s), 7.32-7.31 (m, 3H), 7.23 (s, 1H), 7.19-7.15 (m, 2H), 7.09 (t, J=7.5 Hz, 1H), 6.98 (d, J=7.5 Hz, 1H), 4.64 (s, 1H).

LCMS m/z=244.3 (M+H)

3-(3-chlorophenyl)-3-(3-(trifluoromethoxy)benzyl)indolin-2-one. A mixture of 3-(3-chlorophenyl)indolin-2-one (950 mg, 3.90 mmol) and sodium carbonate (537 mg, 5.07 mmol) in DMA (8 ml) was treated with 1-(bromomethyl)-3-(trifluoromethoxy)benzene (0.696 ml, 4.29 mmol) at 0° C. The reaction was stirred at room temperature until the starting material was completely consumed as indicated by LCMS. The reaction was diluted with ethyl acetate, washed with water (2×), and dried over Na$_2$SO$_4$. The crude solution was concentrated and purified by silica gel chromatography (Biotage 25 g SNAP cartridge; 0-30% ethyl acetate in hexanes) to provide 3-(3-chlorophenyl)-3-(3-(trifluoromethoxy)benzyl)indolin-2-one.

$^1$H NMR (500 MHz) δ 7.50 (s, 1H), 7.42-7.41 (m, 1H), 7.34-7.29 (m, 2H), 7.24-7.21 (m, 2H), 7.14-7.10 (m, 2H), 6.97 (d, J=7.5 Hz, 1H), 6.93 (d, J=7.5 Hz, 1H), 6.75 (d, J=8 Hz, 1H), 6.73 (s, 1H), 3.73 (d, J=13 Hz, 1H), 3.47 (d, J=13 Hz, 1H).

LCMS m/z=418.2 (M+H)

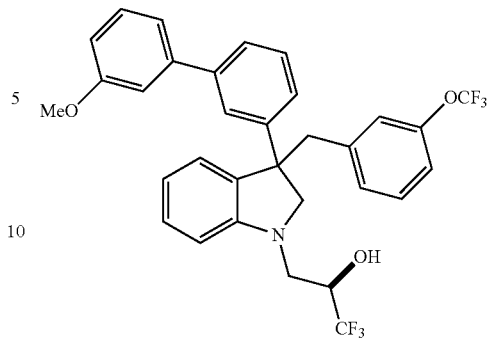

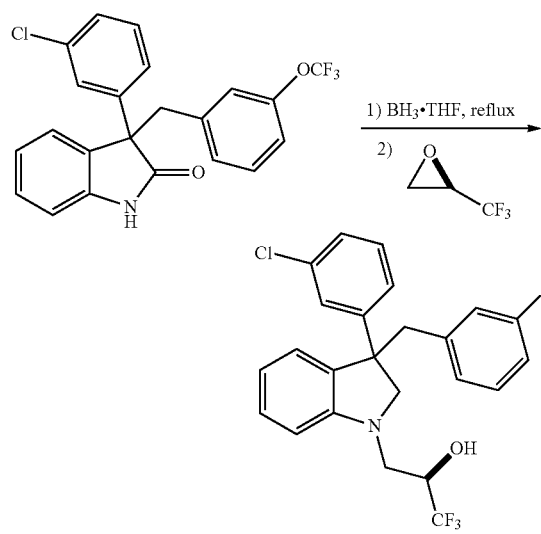

(2R)-3-(3-(3-chlorophenyl)-3-(3-(trifluoromethoxy)benzyl)indolin-1-yl)-1,1,1-trifluoro-propan-2-ol. Borane tetrahydrofuran complex (8.08 ml, 8.08 mmol) was added to a solution of 3-(3-chlorophenyl)-3-(3-(trifluoromethoxy)benzyl)indolin-2-one (1.35 g, 3.23 mmol) in THF (8 ml). The mixture was stirred at 70° C. for 24 h. The reaction was cooled to room temperature and quenched with saturated NH$_4$Cl solution and the product was extracted with ethyl acetate. The extracts were dried over Na$_2$SO$_4$, filtered, and concentrated. The crude material was used directly in the next stage of the sequence as follows. Crude 3-(3-chlorophenyl)-3-(3-(trifluoromethoxy)benzyl)indoline (1.304 g, 3.23 mmol) and (R)-2-(trifluoromethyl)oxirane (0.842 ml, 9.69 mmol) were combined in 1,1,1,3,3,3-hexafluoro-2-propanol (3.40 ml, 32.3 mmol) and stirred overnight at room temperature. The solvent was removed and the crude material was purified by reverse phase chromatography (Biotage 60 g SNAP cartridge (2 injections): 10-90% acetonitrile in water+0.05% TFA) to provide (2R)-3-(3-(3-chlorophenyl)-3-(3-(trifluoromethoxy)benzyl)indolin-1-yl)-1,1,1-trifluoro-propan-2-ol.

$^1$H NMR (500 MHz) (mixture of diastereomers) δ 7.45 (s, 0.5H), 7.42 (s, 0.5H), 7.35-7.29 (m, 3H), 7.23-7.17 (m, 2H), 7.07-7.04 (m, 2H), 6.90-6.87 (m, 1H), 6.80 (d, J=8 Hz, 0.5H), 6.76 (d, J=7.5 Hz, 0.5H), 6.53-6.50 (m, 2H), 3.98 (m, 1H), 3.79 (d, J=9.5 Hz, 0.5H), 3.74 (d, J=9.5 Hz, 0.5H), 3.56 (d, J=9.5 Hz, 0.5H), 3.52 (d, J=9.5 Hz, 0.5H), 3.42-3.27 (m, 3H), 3.18-3.12 (m, 1H), 2.26 (d, J=6 Hz, 0.5H), 2.15 (d, J=4.5 Hz, 0.5H).

LCMS m/z=516.3 (M+H)

Example 25

(2R)-1,1,1-trifluoro-3-(3-(3'-methoxy-[1,1'-biphenyl]-3-yl)-3-(3-(trifluoromethoxy)benzyl)indolin-1-yl)propan-2-ol was prepared from Example 4 as described below.

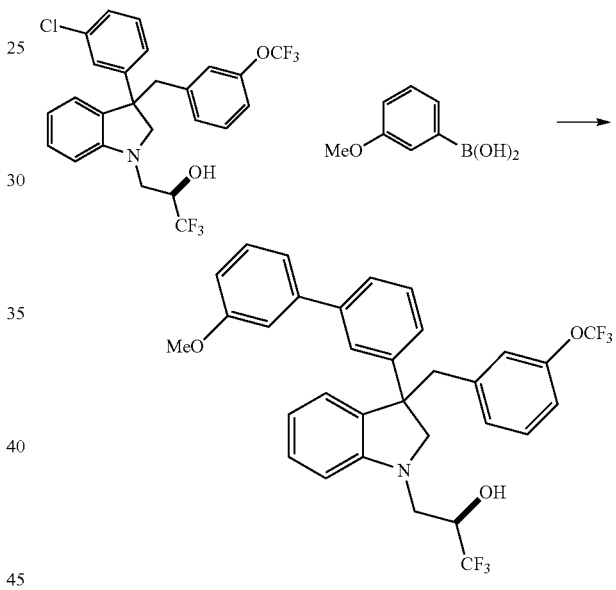

(2R)-3-(3-(3-chlorophenyl)-3-(3-(trifluoromethoxy)benzyl)indolin-1-yl)-1,1,1-trifluoro-propan-2-ol (50 mg, 0.097 mmol), 3-methoxy-phenylboronic acid (44.2 mg, 0.291 mmol), Pd(OAc)$_2$ (2.1 mg, 9.69 μmol), 2-dicyclohexylphosphino-2',6'-dimethoxybiphenyl (5.97 mg, 0.015 mmol), and potassium phosphate tribasic (61.7 mg, 0.291 mmol) were combined in a degassed mixture of toluene (0.3 ml) and water (0.06 ml) and heated to 80° C. for 4 h. The reaction was complete by LCMS at this time. The mixture was cooled, diluted with ethyl acetate, and filtered through silica gel eluting with ethyl acetate. The eluent was concentrated and the material was purified by reverse phase chromatography (Biotage 25 g SNAP C-18 cartridge; 10-90% acetonitrile in water+0.05% TFA) to provide (2R)-1,1,1-trifluoro-3-(3-(3'-methoxy-[1,1'-biphenyl]-3-yl)-3-(3-(trifluoromethoxy)-benzyl)indolin-1-yl)propan-2-ol.

$^1$H NMR (500 MHz) (mixture of diastereomers) δ 7.68 (s, 0.5H), 7.64 (s, 0.5H), 7.52-7.50 (m, 1H), 7.46-7.43 (m, 2H), 7.40-7.37 (m, 1H), 7.23-7.05 (m, 5H), 6.94-6.88 (m, 2H), 6.82 (d, J=7.5 Hz, 0.5H), 6.80 (d, J=7.5 Hz, 0.5H), 6.56-6.51 (m, 2H), 4.00 (broad s, 1H), 3.89 (s, 3H), 3.81 (d, J=13 Hz, 0.5H), 3.79 (d, J=13 Hz, 0.5H), 3.65 (d, J=9.5 Hz, 0.5H), 3.60 (d, J=9.5 Hz, 0.5H), 3.52-3.74 (m, 1H), 3.42-3.38 (m, 1H), 3.37-3.30 (m, 1H), 3.20 (dd, J=15 Hz, J=7.5 Hz, 0.5H), 3.14 (dd, J=14 Hz, J=3.5 Hz, 0.5H), 2.34 (broad s, 0.5H), 2.23 (broad s, 0.5H).

LCMS m/z=588.4 (M+H)

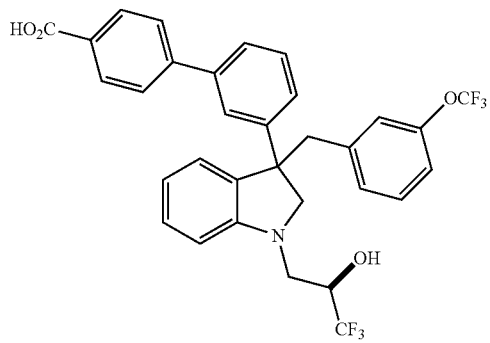 [SMILES: O=C(O)c1ccc(-c2cccc(C3(Cc4cccc(OC(F)(F)F)c4)CN(C[C@@H](O)C(F)(F)F)c4ccccc43)c2)cc1]

Example 26

3'-(1-((R)-3,3,3-trifluoro-2-hydroxypropyl)-3-(3-(trifluoromethoxy)-benzyl)indolin-3-yl)-[1,1'-biphenyl]-4-carboxylic acid was prepared from Example 4 as described below.

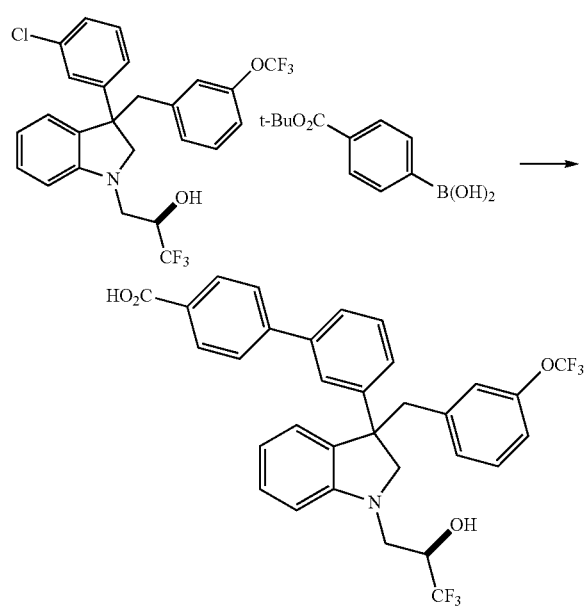

(2R)-3-(3-(3-chlorophenyl)-3-(3-(trifluoromethoxy)benzyl)indolin-1-yl)-1,1,1-trifluoropropan-2-ol (74 mg, 0.143 mmol), (4-(tert-butoxycarbonyl)phenyl)boronic acid (63.7 mg, 0.287 mmol), Pd(OAc)$_2$ (3.22 mg, 0.014 mmol), 2-dicyclohexylphosphino-2',6'-dimethoxybiphenyl (7.07 mg, 0.017 mmol), and potassium phosphate tribasic (91 mg, 0.430 mmol) were combined in a mixture of degassed THF (0.4 ml) and water (0.1 ml) and heated to 75° C. for 14 h. The reaction was diluted with ethyl acetate and filtered through a pad of silica gel eluting with ethyl acetate. The eluent was concentrated and the crude product was dissolved in DCM (1 ml) and treated with TFA (1.0 ml, 12.98 mmol). When the reaction was judged to be complete by LCMS the solvent was removed and the product was purified by reverse phase chromatography (Biotage 30 g C-18 SNAP cartridge; 10-100% ACN in water+0.05% TFA) to provide 3'-(1-((R)-3,3,3-trifluoro-2-hydroxypropyl)-3-(3-(trifluoromethoxy)-benzyl)indolin-3-yl)-[1,1'-biphenyl]-4-carboxylic acid.

$^1$H NMR (500 MHz) (mixture of diastereomers) δ 8.33 (s, 0.5H), 8.31 (s, 0.5H), 8.11 (m, 1H), 7.84-7.78 (m, 1.5H), 7.69 (s, 1H), 7.59-7.47 (m, 4H), 7.21-7.16 (m, 3H), 7.07-7.04 (m, 1H), 6.91-6.82 (m, 2H), 6.61 (s, 0.5H), 6.59 (s, 0.5H), 6.55-6.51 (m, 1H), 4.12-4.03 (broad m, 1H), 3.81-3.70 (m, 2H), 3.61 (d, J=13.5 Hz, 0.5H), 3.57 (d, J=13 Hz, 0.5H), 3.43 (d, J=12.5 Hz, 0.5H), 3.41 (d, J=13 Hz, 0.5H), 3.35-3.24 (m, 2H).

LCMS m/z=602.2 (M+H)

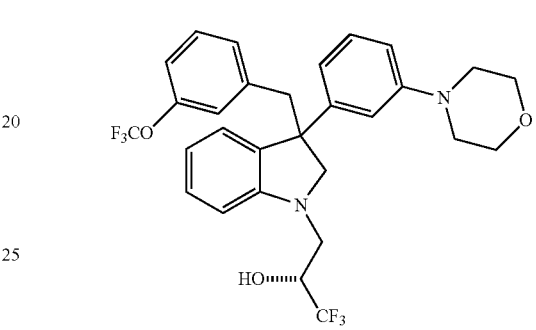

Example 31

(2R)-1,1,1-trifluoro-3-(3-(3-morpholinophenyl)-3-(3-(trifluoromethoxy)benzyl)indolin-1-yl)propan-2-ol was prepared from Example 4 as described below.

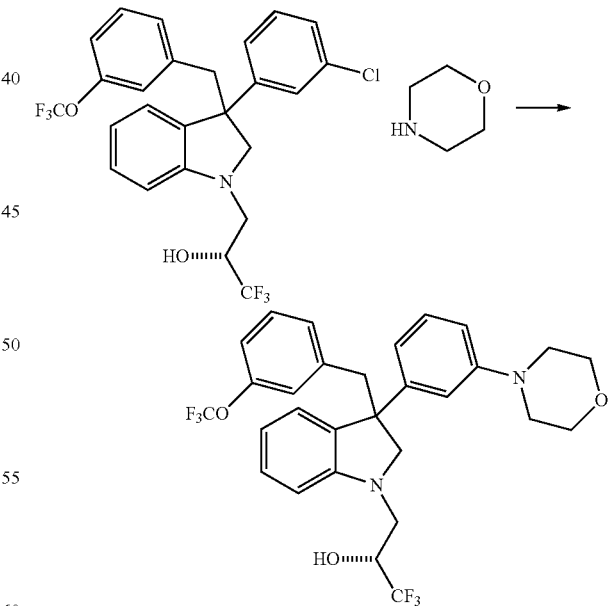

Morpholine (0.025 ml, 0.291 mmol) was added to a solution of (2R)-3-(3-(3-chlorophenyl)-3-(3-(trifluoromethoxy)benzyl)indolin-1-yl)-1,1,1-trifluoro-propan-2-ol (50 mg, 0.097 mmol), sodium tert-pentoxide (32.0 mg, 0.291 mmol), and (2-dicyclohexylphosphino-2',4',6'-triisopropyl-1,1'-biphenyl)[2-(2-aminoethyl)phenyl]palladium (II) chloride (7.16 mg, 9.69 μmol) in degassed dioxane (0.3 ml). The mixture was heated to 80° C. for 4 h. LCMS indicated a complete reaction at this time. The mixture was cooled to room temperature, diluted with ethyl acetate, and filtered through silica gel eluting with ethyl acetate. The eluent was concentrated and purified by reverse phase chromatography (Biotage 30 g C-18 SNAP cartridge; 10-90% acetonitrile in water+0.05% TFA) to provide (2R)-1,1,1-trifluoro-3-(3-(3-morpholinophenyl)-3-(3-(trifluoromethoxy)benzyl)indolin-1-yl)propan-2-ol (41 mg, 75%). Analogous compounds were purified by reverse phase chromatography using a 19×50 mm Sunfire Column with a 50 to 98% MeCN in water gradient+0.1% TFA.

$^1$H NMR (500 MHz) (mixture of diastereomers) δ 7.31-7.27 (m, 1H), 7.22-7.16 (m, 2H), 7.09-7.04 (m, 2H), 7.02-6.96 (m, 2H), 6.89-6.83 (m, 2H), 6.80 (d, J=7.5 Hz, 0.5H), 6.77 (d, J=7.5 Hz, 0.5H), 6.75-6.50 (m, 2H), 3.99 (broad s, 1H), 3.88-3.86 (m, 4H), 3.76 (d, J=12.5 Hz, 0.5H), 3.74 (d, J=13 Hz, 0.5H), 3.58 (d, J=9.5 Hz, 0.5H), 3.52 (d, J=9 Hz, 0.5H), 3.43-3.39 (m, 1H), 3.37-3.29 (m, 2H), 3.20-3.10 (m, 5H), 2.41 (m, 0.5H), 2.30 (m, 0.5H).

LCMS m/z=567.4 (M+H)

| Example no. | Structure | IC$_{50}$ RTA 2% serum (nM) | IC$_{50}$ RTA 95% serum (nM) | LCMS (M + H) |
|---|---|---|---|---|
| Example 25 | 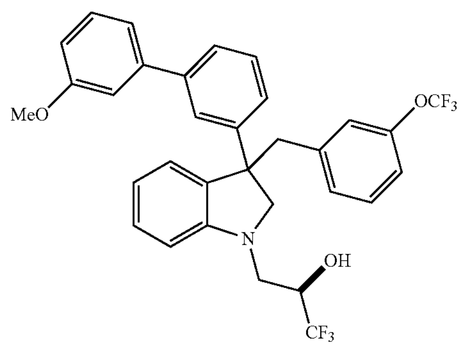 [SMILES: COc1cccc(-c2cccc(C3(Cc4cccc(OC(F)(F)F)c4)CN(C[C@@H](O)C(F)(F)F)c4ccccc43)c2)c1] | 1471 | 3130 | 588.4 |
| Example 26 | 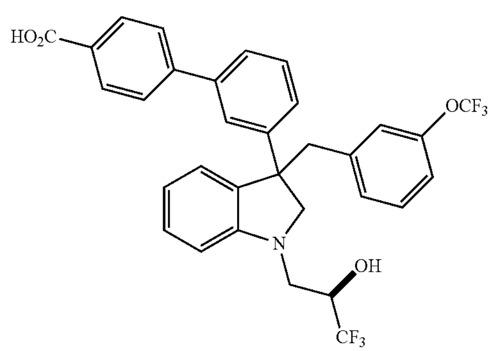 [SMILES: O=C(O)c1ccc(-c2cccc(C3(Cc4cccc(OC(F)(F)F)c4)CN(C[C@@H](O)C(F)(F)F)c4ccccc43)c2)cc1] | 1350 | 3862 | 602.3 |
| Example 27 | 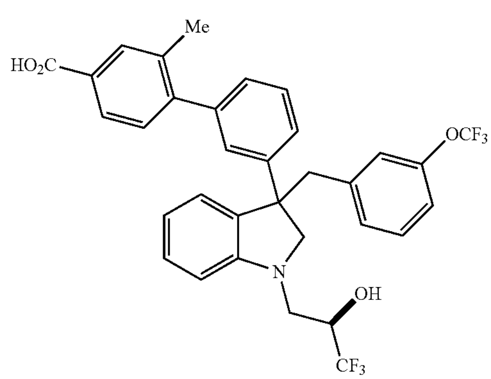 [SMILES: Cc1cc(C(=O)O)ccc1-c1cccc(C2(Cc3cccc(OC(F)(F)F)c3)CN(C[C@@H](O)C(F)(F)F)c3ccccc32)c1] | 378 | 4068 | 616.2 |

-continued
| Example no. | Structure | IC$_{50}$ RTA 2% serum (nM) | IC$_{50}$ RTA 95% serum (nM) | LCMS (M + H) |
|---|---|---|---|---|
| Example 28 | 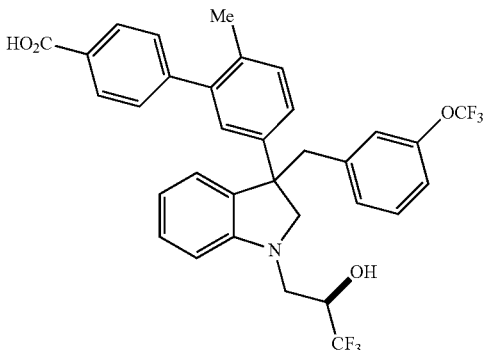 | 1508 | | 616.1 |
| Example 29 | 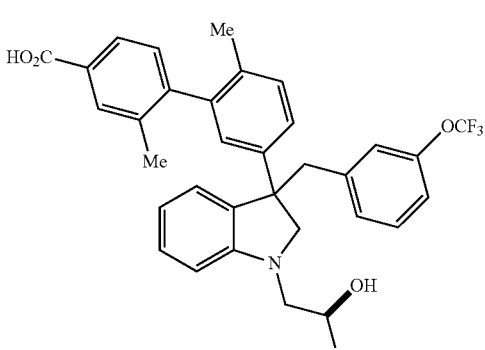 | 1692 | | 630.1 |
| Example 30 | 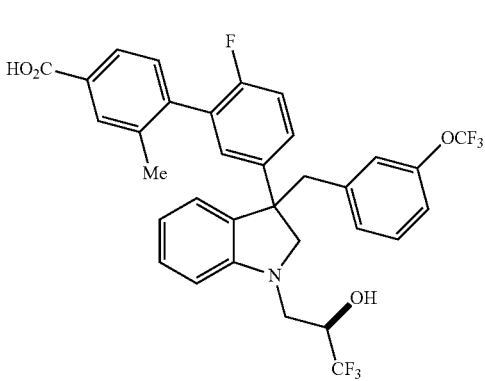 [SMILES: Cc1cc(C(=O)O)ccc1-c1cc(C2(Cc3cccc(OC(F)(F)F)c3)CN(C[C@@H](O)C(F)(F)F)c3ccccc32)ccc1F] | 328 | | 634.1 |
| Example 31 | 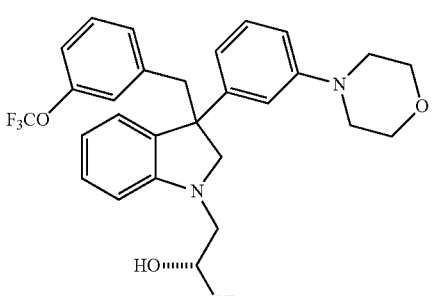 | 146 | 643 | 567.4 |

-continued

| Example no. | Structure | IC$_{50}$ RTA 2% serum (nM) | IC$_{50}$ RTA 95% serum (nM) | LCMS (M + H) |
| --- | --- | --- | --- | --- |
| Example 32 | 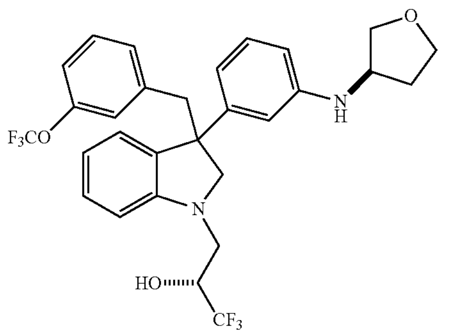 | 252 | 1427 | 567 |
| Example 33 | 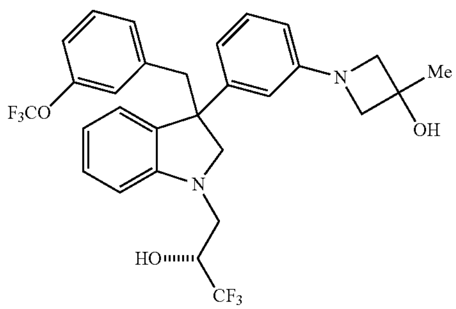 [SMILES: CC1(O)CN(c2cccc(C3(Cc4cccc(OC(F)(F)F)c4)CN(C[C@@H](O)C(F)(F)F)c4ccccc43)c2)C1] | 1234 | 4380 | 567 |
| Example 34 | 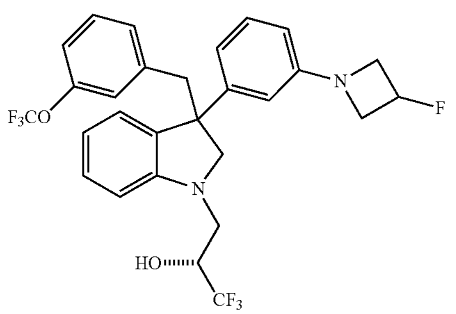 [SMILES: O[C@H](CN1CC(Cc2cccc(OC(F)(F)F)c2)(c2cccc(N3CC(F)C3)c2)c2ccccc21)C(F)(F)F] | 59 | 319 | 555 |
| Example 35 | 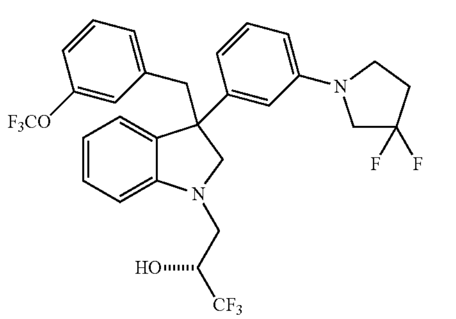 [SMILES: O[C@H](CN1CC(Cc2cccc(OC(F)(F)F)c2)(c2cccc(N3CCC(F)(F)C3)c2)c2ccccc21)C(F)(F)F] | 98 | 533 | 587 |

-continued

| Example no. | Structure | IC$_{50}$ RTA 2% serum (nM) | IC$_{50}$ RTA 95% serum (nM) | LCMS (M + H) |
|---|---|---|---|---|
| Example 36 | 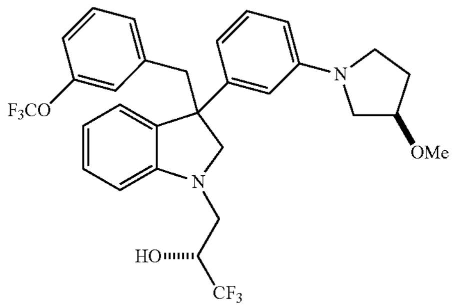 [SMILES: CO[C@@H]1CCN(c2cccc(C3(Cc4cccc(OC(F)(F)F)c4)CN(C[C@@H](O)C(F)(F)F)c4ccccc43)c2)C1] | 115 | 780 | 581 |
| Example 37 | 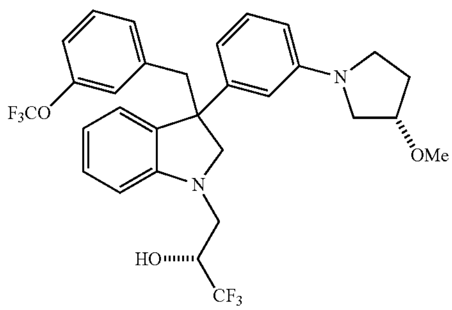 [SMILES: CO[C@H]1CCN(c2cccc(C3(Cc4cccc(OC(F)(F)F)c4)CN(C[C@@H](O)C(F)(F)F)c4ccccc43)c2)C1] | 77 | 395 | 581 |
| Example 38 | 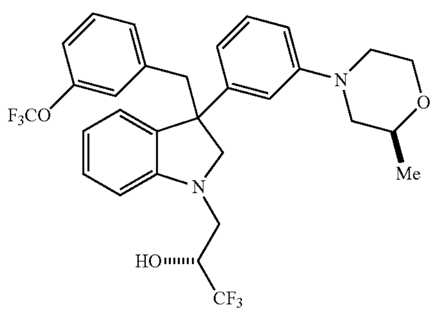 [SMILES: C[C@H]1CN(c2cccc(C3(Cc4cccc(OC(F)(F)F)c4)CN(C[C@@H](O)C(F)(F)F)c4ccccc43)c2)CCO1] | 117 | 674 | 581 |
| Example 39 | 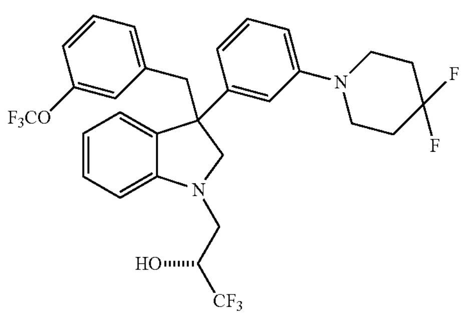 [SMILES: O[C@H](CN1CC(Cc2cccc(OC(F)(F)F)c2)(c2cccc(N3CCC(F)(F)CC3)c2)c2ccccc21)C(F)(F)F] | 164 | 1083 | 601 |
| Example 40 | 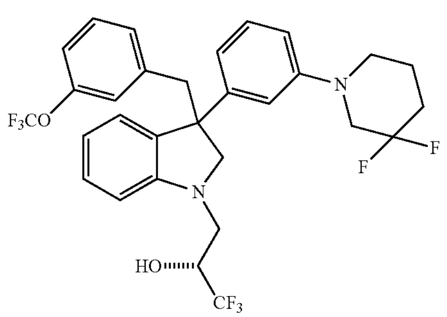 [SMILES: O[C@H](CN1CC(Cc2cccc(OC(F)(F)F)c2)(c2cccc(N3CCCC(F)(F)C3)c2)c2ccccc21)C(F)(F)F] | 119 | 791 | 601 |

| Example no. | Structure | IC$_{50}$ RTA 2% serum (nM) | IC$_{50}$ RTA 95% serum (nM) | LCMS (M + H) |
|---|---|---|---|---|
| Example 41 | 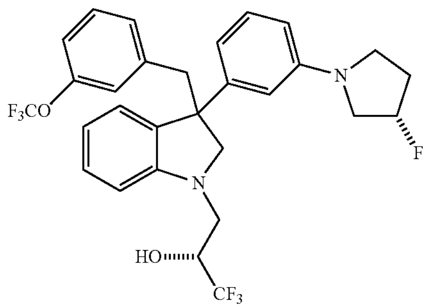 [SMILES: O[C@H](CN1CC(Cc2cccc(OC(F)(F)F)c2)(c2cccc(N3CC[C@H](F)C3)c2)c2ccccc21)C(F)(F)F] | 72 | 498 | 569 |
| Example 42 | 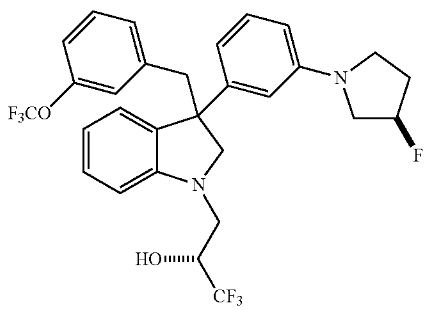 [SMILES: O[C@H](CN1CC(Cc2cccc(OC(F)(F)F)c2)(c2cccc(N3CC[C@@H](F)C3)c2)c2ccccc21)C(F)(F)F] | 40 | 766 | 569 |
| Example 43 | 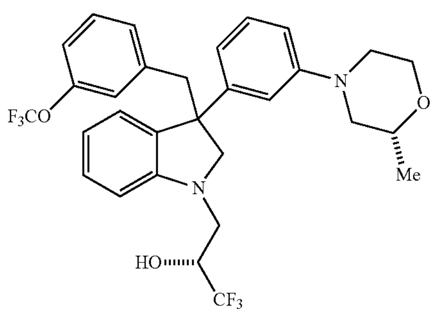 [SMILES: C[C@@H]1CN(c2cccc(C3(Cc4cccc(OC(F)(F)F)c4)CN(C[C@@H](O)C(F)(F)F)c4ccccc43)c2)CCO1] | 97 | 932 | 581 |
| Example 44 | 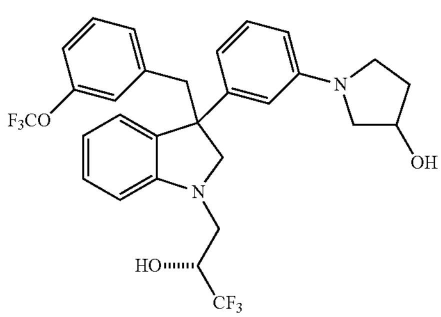 [SMILES: OC1CCN(c2cccc(C3(Cc4cccc(OC(F)(F)F)c4)CN(C[C@@H](O)C(F)(F)F)c4ccccc43)c2)C1] | 489 | 2040 | 567 |

Examples 45-60 were prepared according to Scheme A3. Specific experimental procedures are described below.

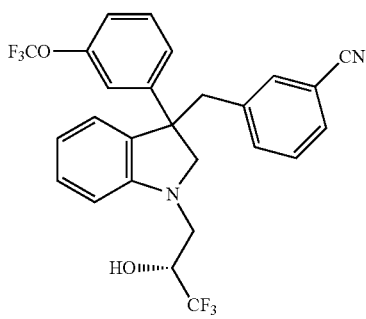 [SMILES: N#Cc1cccc(CC2(c3cccc(OC(F)(F)F)c3)CN(C[C@@H](O)C(F)(F)F)c3ccccc32)c1]

Example 45

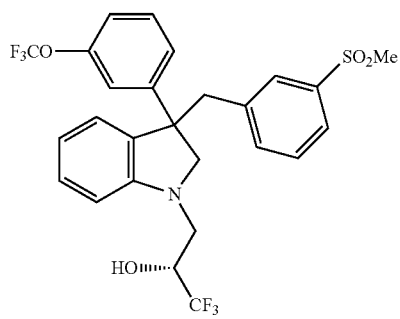 [SMILES: CS(=O)(=O)c1cccc(CC2(c3cccc(OC(F)(F)F)c3)CN(C[C@@H](O)C(F)(F)F)c3ccccc32)c1]

Example 46

3-((1-((R)-3,3,3-trifluoro-2-hydroxypropyl)-3-(3-(trifluoromethoxy)phenyl)indolin-3-yl)methyl)benzonitrile was prepared from Example 3 (prepared according to Scheme A1) as described below.

(2R)-1,1,1-trifluoro-3-(3-(3-(methylsulfonyl)benzyl)-3-(3-(trifluoromethoxy)phenyl)indolin-1-yl)propan-2-ol was prepared from Example 3 (prepared according to Scheme A1) as described below.

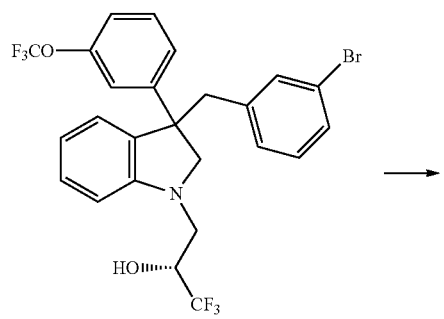

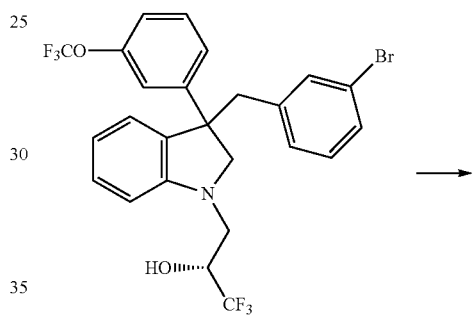

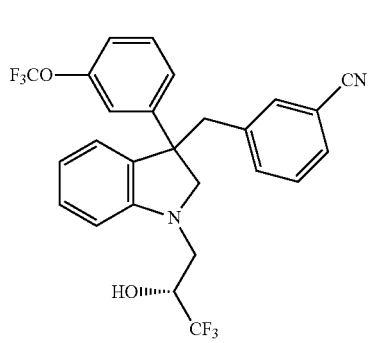

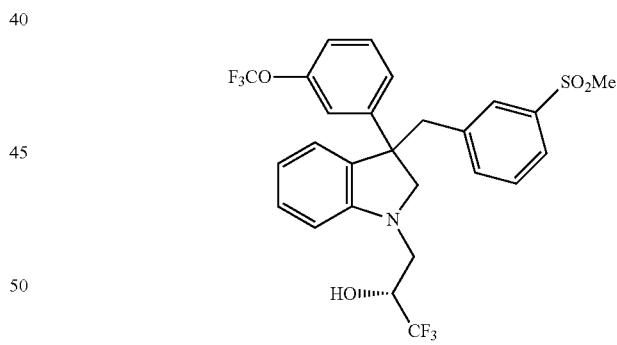

In a reaction vessel was charged (2R)-3-(3-(3-bromobenzyl)-3-(3-(trifluoromethoxy)phenyl)indolin-1-yl)-1,1,1-trifluoropropan-2-ol, Ex. 3, (60 mg, 0.107 mmol), zinc cyanide (42.4 mg, 0.36 mmol) and tetrakis (triphenylphosphine) palladium(0) (18.56 mg, 0.016 mmol) in DMF (1 ml). The reaction vessel was sealed and evacuated and purged with nitrogen. The reaction was heated to 110° C. for 12 hrs. The reaction was diluted with EtOAc and washed with aq. NaHCO₃, brine, dried and concentrated. The crude product was purified by silica gel chromatography to yield 3-((1-((R)-3,3,3-trifluoro-2-hydroxypropyl)-3-(3-(trifluoromethoxy)phenyl)indolin-3-yl)methyl)-benzonitrile (20 mg, 0.039 mmol).

In a reaction vessel was charged (2R)-3-(3-(3-bromobenzyl)-3-(3-(trifluoromethoxy)phenyl)indolin-1-yl)-1,1,1-trifluoropropan-2-ol, Ex. 3, (60 mg, 0.107 mmol), methanesulfinic acid sodium salt (24.05 mg, 0.24 mmol), L-proline (49.3 mg, 0.428 mmol) and CuI (40.8 mg, (0.21 mmol) in DMSO (1 ml). The reaction vessel was sealed and evacuated and purged with nitrogen. The reaction was heated to 110° C. for 12 hrs. The reaction was diluted with EtOAc and washed with aq. NaHCO₃ and brine, then was dried and concentrated. The residue was purified by silica gel chromatography to yield (2R)-1,1,1-trifluoro-3-(3-(3-(methylsulfonyl)-benzyl)-3-(3-(trifluoromethoxy)phenyl)indolin-1-yl)propan-2-ol.

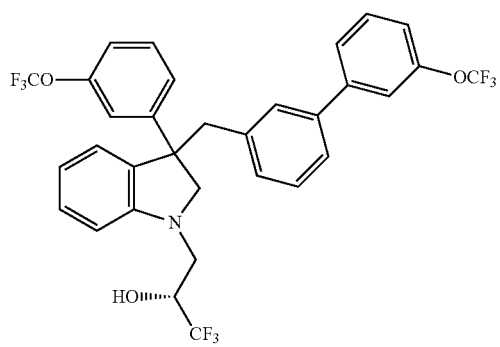 [SMILES: O[C@H](CN1CC(Cc2cccc(-c3cccc(OC(F)(F)F)c3)c2)(c2cccc(OC(F)(F)F)c2)c2ccccc21)C(F)(F)F]

Example 47

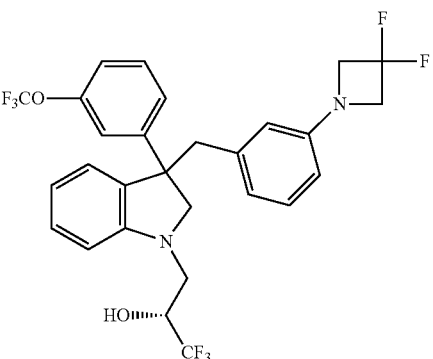

Example 48

(2R)-1,1,1-trifluoro-3-(3-((3'-(trifluoromethoxy)-[1,1'-biphenyl]-3-yl)methyl)-3-(3-(trifluoromethoxy)phenyl)indolin-1-yl)propan-2-ol was prepared from the compound of Example 3 (prepared according to Scheme A1) as described below.

(2R)-3-(3-(3-(3,3-difluoroazetidin-1-yl)benzyl)-3-(3-(trifluoromethoxy)phenyl)indolin-1-yl)-1,1,1-trifluoropropan-2-ol was prepared from Example 3 (prepared according to Scheme A1) as described below. Examples 49-60 were prepared in a similar fashion.

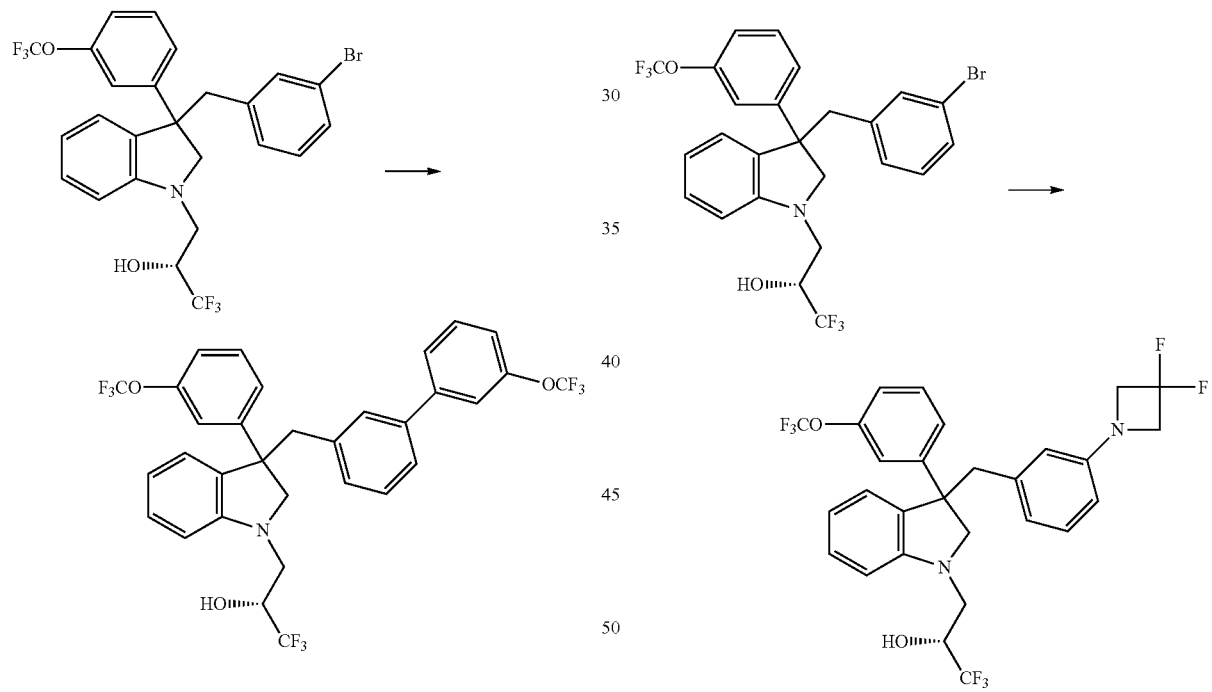

In a reaction vessel was charged (2R)-3-(3-(3-bromobenzyl)-3-(3-(trifluoromethoxy)phenyl)indolin-1-yl)-1,1,1-trifluoropropan-2-ol, Ex. 3 (50 mg, 0.089 mmol), (3-(trifluoromethoxy)phenyl)boronic acid (24 mg, 0.116 mmol), Pd(OAc)$_2$ (2 mg, 0.089 mmol), SPhos (40.8 mg, (5.5 mg, 0.013 mmol) and K$_3$PO$_4$ (38 mg, 0.089 mmol) in 3:1 THF:water (0.3 ml). The reaction vessel was sealed and evacuated and purged with nitrogen. The reaction was heated to 65° C. for 1 hr. The reaction was diluted with EtOAc and washed with aqueous NaHCO$_3$ and brine, then was dried and concentrated. The residue was purified by silica gel chromatography to yield (2R)-1,1,1-trifluoro-3-(3-((3'-(trifluoro-methoxy)-[1,1'-biphenyl]-3-yl)methyl)-3-(3-(trifluoromethoxy)phenyl)indolin-1-yl)propan-2-ol.

In a reaction vessel was charged (2R)-3-(3-(3-bromobenzyl)-3-(3-(trifluoromethoxy)phenyl)indolin-1-yl)-1,1,1-trifluoropropan-2-ol (70 mg, 0.125 mmol), 3,3-difluoroazetidine HCl (19.4 mg, 0.15 mmol), RuPhos precatalyst (9.5 mg, 0.012 mmol), and NaOt-Bu (24 mg, 0.250 mmol) in dioxane (0.4 ml). The reaction vessel was sealed and evacuated and purged with nitrogen. The reaction was heated to 75° C. for 1 hr. The reaction was diluted with EtOAc and washed with aq. NaHCO$_3$, brine, dried and concentrated. The residue was then purified by silica gel chromatography to yield (2R)-3-(3-(3-(3,3-difluoroazetidin-1-yl)benzyl)-3-(3-(trifluoromethoxy)-phenyl)indolin-1-yl)-1,1,1-trifluoropropan-2-ol.

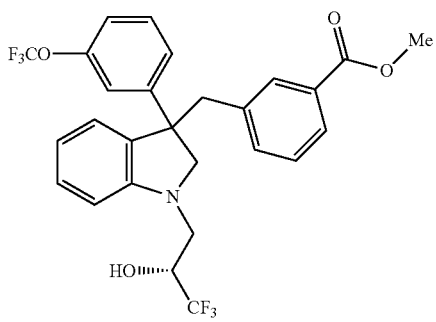

Example 60

Methyl 3-((1-((R)-3,3,3-trifluoro-2-hydroxypropyl)-3-(3-(trifluoromethoxy)phenyl)indolin-3-yl)methyl)benzoate was prepared from Example 3 (prepared according to Scheme A1) as described below.

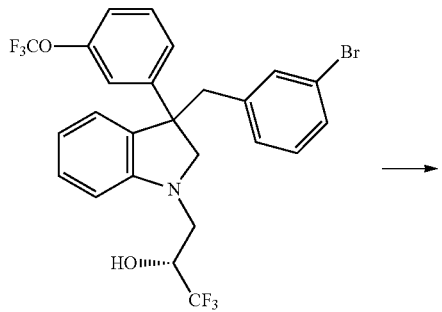

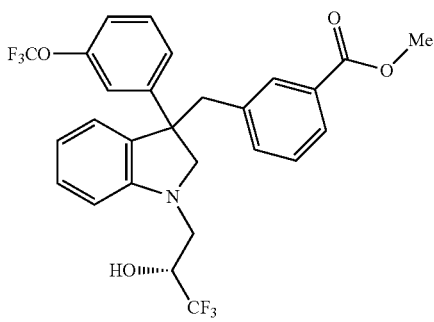 [SMILES: COC(=O)c1cccc(CC2(c3cccc(OC(F)(F)F)c3)CN(C[C@@H](O)C(F)(F)F)c3ccccc32)c1]

In a reaction vessel was charged (2R)-3-(3-(3-bromobenzyl)-3-(3-(trifluoromethoxy)phenyl)indolin-1-yl)-1,1,1-trifluoropropan-2-ol (100 mg, 0.178 mmol), Pd(OAc)$_2$ (4 mg, 0.02 mmol), XantPhos (20.6 mg, 0.036 mmol) in triethylamine (2 ml) and MeOH (0.05 ml). The reaction vessel was sealed and evacuated and purged with CO. The reaction was heated to 75° C. for 12 hrs under an atmosphere of CO (20 psi). The reaction was diluted with EtOAc and washed with aq. NaHCO$_3$, brine, dried and concentrated. The residue was purified by silica gel chromatography to yield methyl 3-((1-((R)-3,3,3-trifluoro-2-hydroxypropyl)-3-(3-(trifluoromethoxy)phenyl)indolin-3-yl)methyl)benzoate.

| Example no. | Structure | IC$_{50}$ RTA 2% serum (nM) | IC$_{50}$ RTA 95% serum (nM) | LCMS (M + H) |
|---|---|---|---|---|
| Example 45 | 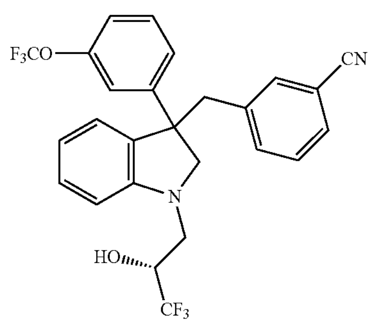 [SMILES: N#Cc1cccc(CC2(c3cccc(OC(F)(F)F)c3)CN(C[C@@H](O)C(F)(F)F)c3ccccc32)c1] | 171 | 917 | 507 |
| Example 46 | 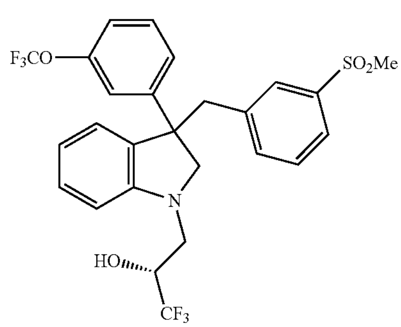 [SMILES: CS(=O)(=O)c1cccc(CC2(c3cccc(OC(F)(F)F)c3)CN(C[C@@H](O)C(F)(F)F)c3ccccc32)c1] | 264 | 8958 | 560 |

| Example no. | Structure | IC$_{50}$ RTA 2% serum (nM) | IC$_{50}$ RTA 95% serum (nM) | LCMS (M + H) |
|---|---|---|---|---|
| Example 47 | 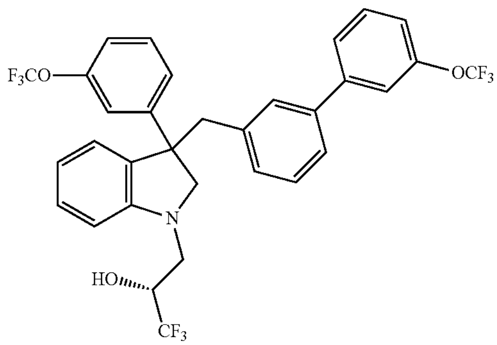 [SMILES: O[C@H](CN1CC(Cc2cccc(-c3cccc(OC(F)(F)F)c3)c2)(c2cccc(OC(F)(F)F)c2)c2ccccc21)C(F)(F)F] | 720 | 2880 | 642 |
| Example 48 | 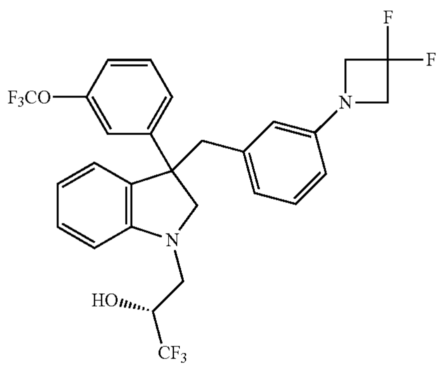 [SMILES: O[C@H](CN1CC(Cc2cccc(N3CC(F)(F)C3)c2)(c2cccc(OC(F)(F)F)c2)c2ccccc21)C(F)(F)F] | 83 | 246 | 573 |
| Example 49 | 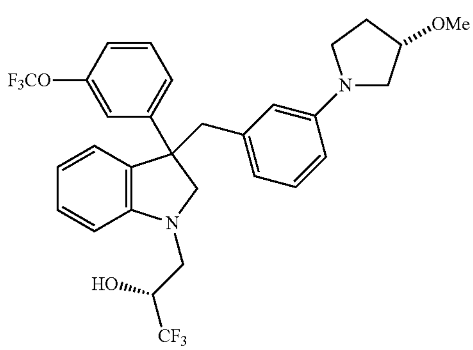 [SMILES: CO[C@H]1CCN(c2cccc(CC3(c4cccc(OC(F)(F)F)c4)CN(C[C@@H](O)C(F)(F)F)c4ccccc43)c2)C1] | 197 | 2095 | 581 |
| Example 50 | 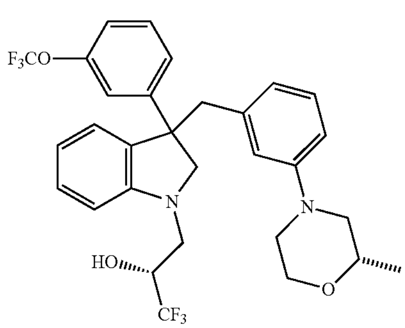 [SMILES: C[C@H]1CN(c2cccc(CC3(c4cccc(OC(F)(F)F)c4)CN(C[C@@H](O)C(F)(F)F)c4ccccc43)c2)CCO1] | 474 | 4934 | 581 |

-continued

| Example no. | Structure | IC$_{50}$ RTA 2% serum (nM) | IC$_{50}$ RTA 95% serum (nM) | LCMS (M + H) |
| --- | --- | --- | --- | --- |
| Example 51 | 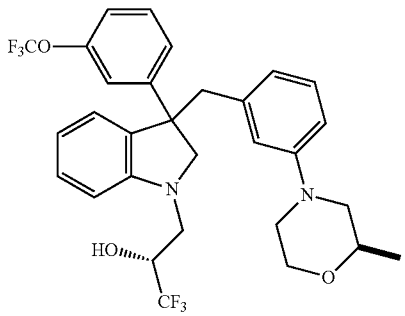 [SMILES: C[C@@H]1CN(c2cccc(CC3(c4cccc(OC(F)(F)F)c4)CN(C[C@@H](O)C(F)(F)F)c4ccccc43)c2)CCO1] | 1610 | 1720 | 581 |
| Example 52 | 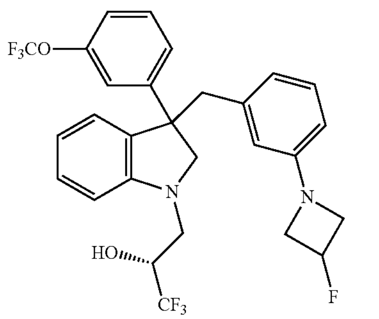 [SMILES: O[C@H](CN1CC(Cc2cccc(N3CC(F)C3)c2)(c2cccc(OC(F)(F)F)c2)c2ccccc21)C(F)(F)F] | 447 | 5836 | 555 |
| Example 53 | 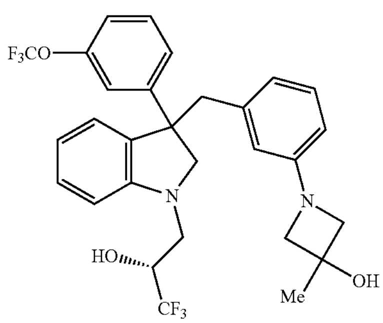 [SMILES: CC1(O)CN(c2cccc(CC3(c4cccc(OC(F)(F)F)c4)CN(C[C@@H](O)C(F)(F)F)c4ccccc43)c2)C1] | 680 | 8053 | 567 |
| Example 54 | 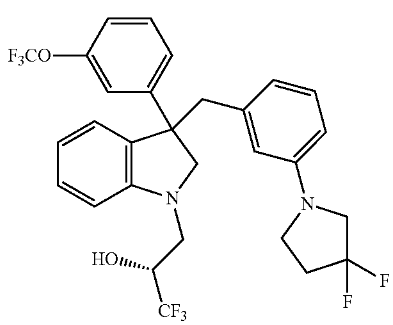 [SMILES: O[C@H](CN1CC(Cc2cccc(N3CCC(F)(F)C3)c2)(c2cccc(OC(F)(F)F)c2)c2ccccc21)C(F)(F)F] | 510 | 3650 | 587 |

-continued

| Example no. | Structure | IC$_{50}$ RTA 2% serum (nM) | IC$_{50}$ RTA 95% serum (nM) | LCMS (M + H) |
|---|---|---|---|---|
| Example 55 | 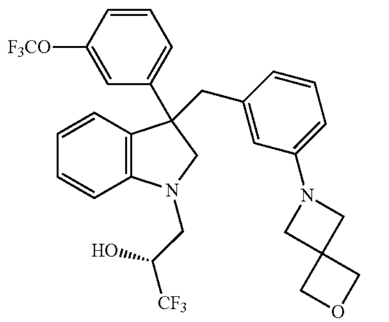 [SMILES: O[C@H](CN1CC(Cc2cccc(N3CC4(COC4)C3)c2)(c2cccc(OC(F)(F)F)c2)c2ccccc21)C(F)(F)F] | 98 | 533 | 579 |
| Example 56 | 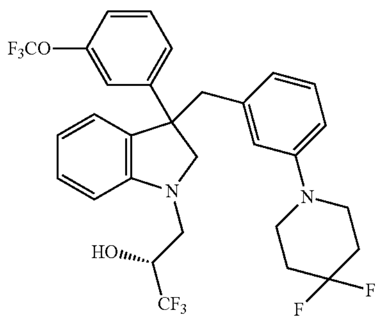 [SMILES: O[C@H](CN1CC(Cc2cccc(N3CCC(F)(F)CC3)c2)(c2cccc(OC(F)(F)F)c2)c2ccccc21)C(F)(F)F] | 413 | 6937 | 601 |
| Example 57 | 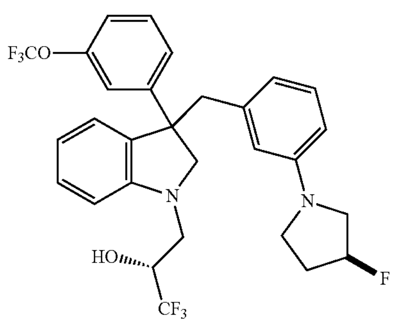 [SMILES: O[C@H](CN1CC(Cc2cccc(N3CC[C@H](F)C3)c2)(c2cccc(OC(F)(F)F)c2)c2ccccc21)C(F)(F)F] | 350 | 3676 | 569 |
| Example 58 | 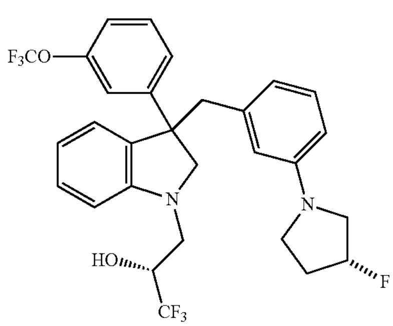 [SMILES: O[C@H](CN1CC(Cc2cccc(N3CC[C@@H](F)C3)c2)(c2cccc(OC(F)(F)F)c2)c2ccccc21)C(F)(F)F] | 171 | 1408 | 569 |

| Example no. | Structure | IC$_{50}$ RTA 2% serum (nM) | IC$_{50}$ RTA 95% serum (nM) | LCMS (M + H) |
|---|---|---|---|---|
| Example 59 | 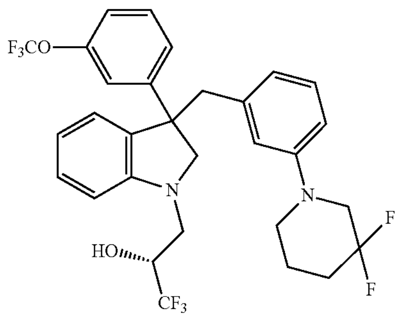 [SMILES: O[C@H](CN1CC(Cc2cccc(N3CCCC(F)(F)C3)c2)(c2cccc(OC(F)(F)F)c2)c2ccccc21)C(F)(F)F] | 198 | 1420 | 601 |
| Example 60 | 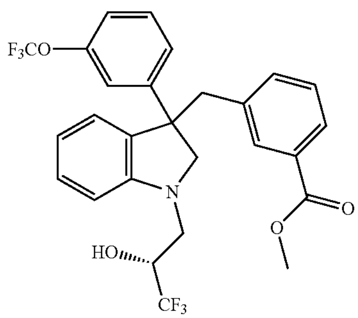 [SMILES: COC(=O)c1cccc(CC2(c3cccc(OC(F)(F)F)c3)CN(C[C@@H](O)C(F)(F)F)c3ccccc32)c1] | 668 | 937 | 540 |

What is claimed is:

1. A compound of Formula I, or a pharmaceutically acceptable salt thereof:

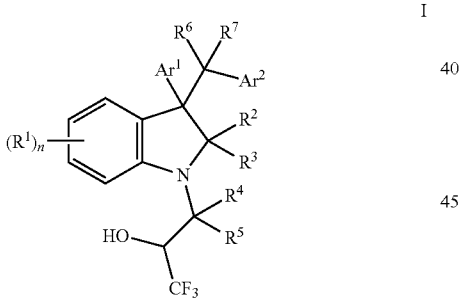

Wherein 1-2 carbon atoms in the phenyl ring of Formula I are optionally replaced with 1-2 heteroatoms selected from NH, S, and O to create a 5-6 membered heteroaromatic ring, wherein:

Each $R^1$ is independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^9R^{10}$, —$CO_2R^8$, —$C(O)NR^9R^{10}$, —$SO_2NR^9R^{10}$, HET(1), phenyl, or $C_{3-6}$ cycloalkyl optionally having 1-2 double bonds, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are each optionally substituted with 1-9 halogens, and wherein HET(1), phenyl, and $C_{3-6}$ cycloalkyl optionally having 1-2 double bonds are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$alkynyl, and —$OC_2$-$C_3$ alkynyl are each optionally substituted with 1-7 halogens;

$R^2$, $R^3$, $R^4$, $R^5$, $R^6$, and $R^7$ are each independently H, —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^9R^{10}$, —$CO_2R^8$, —$C(O)NR^9R^{10}$, —$SO_2NR^9R^{10}$, HET(1), phenyl, or $C_{3-6}$ cycloalkyl optionally having 1-2 double bonds, wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, and —$OC_2$-$C_5$ alkynyl are each optionally substituted with 1-9 halogens, and wherein HET(1), phenyl, and $C_{3-6}$ cycloalkyl optionally having 1-2 double bonds, are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, and —$OC_2$-$C_3$ alkynyl are each optionally substituted with 1-7 halogens;

$R^8$ is H or —$C_{1-5}$alkyl optionally substituted with 1-9 halogens;

$R^9$ and $R^{10}$ are each independently H, —$C_1$-$C_5$ alkyl, —$C_2$-$C_5$ alkenyl, —$C_2$-$C_5$ alkynyl, phenyl, $C_{3-6}$ cycloalkyl optionally having 1-2 double bonds, or HET(1), wherein phenyl, $C_{3-6}$ cycloalkyl optionally having 1-2 double bonds, and HET(1) are optionally substituted with 1-3 substituent groups which are each independently halogen, —$C_1$-$C_3$ alkyl, —$OC_1$-$C_3$ alkyl, —$C_2$-$C_3$ alkenyl, —$OC_2$-$C_3$ alkenyl, —$C_2$-$C_3$ alkynyl, or —$OC_2$-$C_3$ alkynyl, wherein —$C_1$-$C_3$ alkyl, —$OC_1$-$C_3$ alkyl, —$C_2$-$C_3$ alkenyl, —$OC_2$-$C_3$ alkenyl, —$C_2$-$C_3$alkynyl, and —$OC_2$-$C_3$ alkynyl are each optionally substituted with 1-7 halogens;

HET(1) is a 3-7 membered heterocyclic or heteroaromatic ring having 1-4 heteroatoms or heteroatom groups which are each independently N, NH, O, S, S(O), or $S(O)_2$ and optionally having 1-3 double bonds;

$Ar^1$ and $Ar^2$ are each independently phenyl, naphthyl, $C_{3-6}$ cycloalkyl optionally having 1-2 double bonds, or HET(1), wherein $Ar^1$ and $Ar^2$ are each optionally substituted with 1-5 substituents which are independently —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —OH, halogen, —CN, —$NR^9R^{10}$, —$CO_2R^8$, —$SO_2C_1$-$C_5$alkyl, —$C(O)C_1$-$C_5$ alkyl, —$C(O)NR^9R^{10}$, —$SO_2NR^9R^{10}$, or —$NR^9C(O)NR^9R^{10}$, and optionally 1-2 substituents which are phenyl, $C_{3-6}$ cycloalkyl optionally having 1-2 double bonds, HET (1), or HET(2), wherein —$C_1$-$C_5$ alkyl, —$OC_1$-$C_5$ alkyl, —$C_2$-$C_5$ alkenyl, —$OC_2$-$C_5$ alkenyl, —$C_2$-$C_5$ alkynyl, —$OC_2$-$C_5$ alkynyl, —$SO_2C_1$-$C_5$alkyl, and —$C(O)C_1$-$C_5$ alkyl are optionally substituted with 1-9 halogens, and wherein when phenyl, $C_{3-6}$ cycloalkyl optionally having 1-2 double bonds, HET(1), and HET (2) are substituents on $Ar^1$ and $Ar^2$, then phenyl, $C_{3-6}$ cycloalkyl optionally having 1-2 double bonds, HET (1), and HET(2) are optionally substituted with 1-3 substituent groups which are each independently halogen, —OH, —CN, —$NR^9R^{10}$, —$CO_2R^8$, —$C_1$-$C_3$ alkyl, or —$OC_1$-$C_3$ alkyl, wherein —$C_1$-$C_3$ alkyl and —$OC_1$-$C_3$ alkyl are optionally substituted with 1-7 halogens and optionally with 1-2 groups which are —OH, halogen, —CN, —$NR^9R^{10}$, and —$CO_2R^8$;

HET(2) is a bicyclic or spirocyclic heterocycle having two 3-6 membered heterocyclic rings which are fused or are connected through a single carbon atom to make a spirocyclic connection, wherein HET(2) has 2-4 heteroatoms or heteroatom groups which are O, S, $S(O)_2$, N, or NH, and optionally comprises 1-2 double bonds; and n is 0 or an integer from 1-4.

2. The compound of claim 1, or a pharmaceutically acceptable salt thereof, wherein The phenyl ring in Formula I has no optional heteroatoms;

Each $R^1$ is independently —$C_1$-$C_5$ alkyl, —$OC_1$-$C_5$ alkyl, —OH, halogen, —CN, —$NR^9R^{10}$, —$CO_2R^8$, —$C(O)NR^9R^{10}$, —$SO_2NR^9R^{10}$, phenyl, or $C_{3-6}$ cycloalkyl, wherein —$C_1$-$C_5$ alkyl and —$OC_1$-$C_5$ alkyl are each optionally substituted with 1-9 halogens, and wherein phenyl and $C_{3-6}$ cycloalkyl are each optionally substituted with 1-3 groups which are independently halogen, —$C_1$-$C_3$ alkyl, or —$OC_1$-$C_3$ alkyl, wherein —$C_1$-$C_3$ alkyl and —$OC_1$-$C_3$ are each optionally substituted with 1-7 halogens;

$R^2$, $R^3$, $R^4$, $R^5$, $R^6$, and $R^7$ are each independently H, —$C_1$-$C_5$ alkyl, —$OC_1$-$C_5$ alkyl, —OH, halogen, —CN, —$NR^9R^{10}$, —$CO_2R^8$, —$C(O)NR^9R^{10}$, or —$SO_2NR^9R^{10}$, wherein —$C_1$-$C_5$ alkyl and —$OC_1$-$C_5$ alkyl are each optionally substituted with 1-9 halogens;

$R^8$ is H or —$C_{1-5}$alkyl optionally substituted with 1-9 halogens;

$R^9$ and $R^{10}$ are each independently H, —$C_1$-$C_5$ alkyl, phenyl, $C_{3-6}$ cycloalkyl, or HET(1), wherein phenyl, $C_{3-6}$ cycloalkyl, and HET(1) are optionally substituted with 1-3 substituent groups which are each independently halogen, —$C_1$-$C_3$ alkyl, or —$OC_1$-$C_3$ alkyl, wherein —$C_1$-$C_3$ alkyl and —$OC_1$-$C_3$ alkyl are each optionally substituted with 1-7 halogens;

HET(1) is a 3-7 membered heterocyclic or heteroaromatic ring having 1-4 heteroatoms or heteroatom groups which are each independently N, NH, O, S, S(O), or $S(O)_2$ and optionally having 1-3 double bonds;

$Ar^1$ and $Ar^2$ are each independently phenyl, $C_{3-6}$ cycloalkyl, or HET(1), wherein $Ar^1$ and $Ar^2$ are each optionally substituted with 1-5 substituents which are independently —$C_1$-$C_3$ alkyl, —$OC_1$-$C_3$alkyl, —OH, halogen, —CN, —$NR^9R^{10}$, —$CO_2R^8$, —$SO_2C_1$-$C_5$alkyl, —$C(O)C_1$-$C_5$ alkyl, —$C(O)NR^9R^{10}$, —$SO_2NR^9R^{10}$, or —$NR^9C(O)NR^9R^{10}$, and optionally one substituent which is phenyl, $C_{3-6}$ cycloalkyl, HET (1), or HET(2), wherein —$C_1$-$C_3$alkyl, —$OC_1$-$C_3$ alkyl, —$SO_2C_1$-$C_5$alkyl, and —$C(O)C_1$-$C_5$ alkyl are optionally substituted with 1-7 halogens, and wherein when phenyl, $C_{3-6}$ cycloalkyl, HET(1), and HET(2) are substituents on $Ar^1$ and $Ar^2$, then phenyl, $C_{3-6}$ cycloalkyl, HET(1), and HET(2) are optionally substituted with 1-3 substituent groups which are each independently halogen, —OH, —CN, —$NR^9R^{10}$, —$CO_2R^8$, —$C_1$-$C_3$ alkyl, or —$OC_1$-$C_3$ alkyl, wherein —$C_1$-$C_3$ alkyl and —$OC_1$-$C_3$ alkyl are optionally substituted with 1-7 halogens;

HET(2) is a bicyclic or spirocyclic heterocycle having two 3-6 membered heterocyclic rings which are fused or are connected through a single carbon atom to make a spirocyclic connection, wherein HET(2) has 2-4 heteroatoms or heteroatom groups which are O, S, $S(O)_2$, N, or NH, and optionally comprises 1-2 double bonds; and n is 0 or an integer from 1-4.

3. The compound of claim 2, or a pharmaceutically acceptable salt thereof, wherein Each $R^1$ is independently halogen, —$C_1$-$C_4$ alkyl, or —$OC_1$-$C_4$ alkyl, wherein —$C_1$-$C_4$ alkyl and —$OC_1$-$C_4$ alkyl are each optionally substituted with 1-9 halogens;

$R^2$, $R^3$, $R^4$, $R^5$, $R^6$, and $R^7$ are each independently H, halogen, —$C_1$-$C_4$ alkyl or —$OC_1$-$C_4$ alkyl, wherein —$C_1$-$C_4$ alkyl and —$OC_1$-$C_4$ alkyl are optionally substituted with 1-9 halogens;

$R^8$ is H or —$C_{1-4}$alkyl optionally substituted with 1-9 halogens;

$R^9$ is H or —$C_1$-$C_4$ alkyl;

$R^{10}$ is H, —$C_1$-$C_4$ alkyl, or HET(1); and n is 0, 1, 2 or 3.

4. The compound of claim 3, or a pharmaceutically acceptable salt thereof, wherein Each $R^1$ is independently halogen, —$C_1$-$C_3$ alkyl, or —$OC_1$-$C_3$ alkyl, wherein —$C_1$-$C_3$ alkyl and —$OC_1$-$C_3$ alkyl are optionally substituted with 1-7 halogens which are F or Cl;

$R^2$, $R^3$, $R^4$, $R^5$, $R^6$, and $R^7$ are each independently H, halogen, —$C_1$-$C_3$ alkyl or —$OC_1$-$C_3$ alkyl, wherein —$C_1$-$C_3$ alkyl and —$OC_1$-$C_3$ alkyl are optionally substituted with 1-7 halogens which are F or Cl;

$R^8$ is H or —$C_{1-3}$alkyl optionally substituted with 1-7 halogens;

$R^9$ is H or —$C_1$-$C_3$ alkyl; and $R^{10}$ is H, —$C_1$-$C_3$ alkyl, or a 5-6-membered heterocycle having 1-2 heteroatoms which are each O or S, and optionally 1-3 double bonds; and n is 0, 1 or 2.

5. The compound of claim 4, or a pharmaceutically acceptable salt thereof, wherein Each $R^1$ is halogen, —$CH_3$, —$CF_3$, —$OCH_3$, or —$OCF_3$;

$R^2$, $R^3$, $R^4$, $R^5$, $R^6$, and $R^7$ are each independently H, halogen, —$C_1$-$C_2$ alkyl or —$OC_1$-$C_2$ alkyl, wherein —$C_1$-$C_2$ alkyl and —$OC_1$-$C_2$ alkyl are each optionally substituted with 1-5 halogens which are F;

$R^8$ is H or —$CH_3$;

$R^9$ is H or —$CH_3$; and $R^{10}$ is H, —$C_1$-$C_2$alkyl, or a 5-6-membered heterocycle having one heteroatom which is O or S and optionally one double bond.

6. The compound of claim 5, or a pharmaceutically acceptable salt thereof, wherein $R^1$ is —$CH_3$ or F;

$R^2$, $R^3$, $R^4$, $R^5$, $R^6$, and $R^7$ are each H;

$R^8$ is H or —$CH_3$ $R^9$ is H or —$CH_3$;

$R^{10}$ is H, —$CH_3$ or a 5-6-membered saturated heterocycle having 1 heteroatom which is S or O; and n is 0 or 1.

7. The compound of claim 6, or a pharmaceutically acceptable salt thereof, wherein $Ar^1$ and $Ar^2$ are each independently:

(a) Phenyl optionally substituted with 1-2 groups which are independently F, Cl, Br, —CN, —$CH_3$ optionally substituted with 1-3 F, —$OC_{1-2}$ alkyl optionally substituted with 1-5 F, —$OCH(CH_3)_2$, —$CO_2R^8$, or —$SO_2CH_3$, wherein phenyl is optionally substituted with one group phenyl which is optionally substituted with 1-2 groups which are independently —$CH_3$, —$CF_3$, —$OCH_3$, —$OCF_3$, F or —$CO_2R$;

(b) Phenyl optionally substituted with 1-2 groups which are independently halogen, —$CH_3$, —$CF_3$, —$OCH_3$, or —$OCF_3$, wherein phenyl is substituted with —NH-tetrahydrofuryl or with a N-containing heterocycle attached through the N of the heterocycle, wherein the heterocycle is pyrrolidinyl, piperidinyl, azetidinyl, morpholino, or 2-oxa-6-azaspiro[3,3]heptane, wherein the N-containing heterocycle in all cases is optionally substituted with 1-2 groups which are F, —OH, —$CH_3$, —$CF_3$, —$OCH_3$, or —$OCF_3$;

(c) Pyridinyl optionally substituted with one group morpholino and optionally 1-2 groups which are independently F, Cl, —$CH_3$, —$CF_3$, or —$OC_{1-3}$alkyl optionally substituted with 1-7 F; or (d) 2-Thiazolyl optionally substituted with one group which is —$CH_3$, —$CF_3$, —$OCH_3$, —$OCF_3$, or F.

8. A compound, or a pharmaceutically acceptable salt thereof, having the structure below:

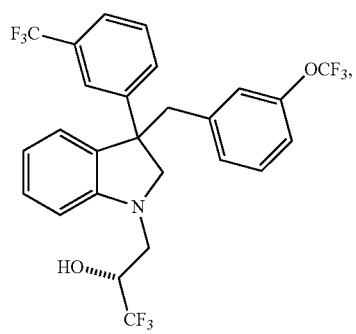

1

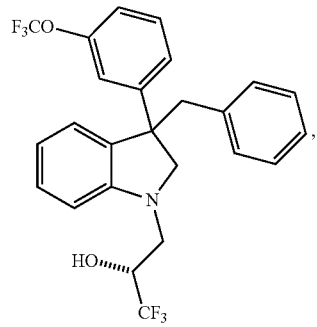

2

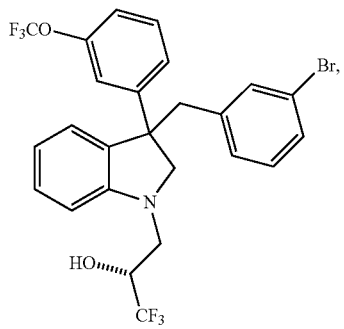

3

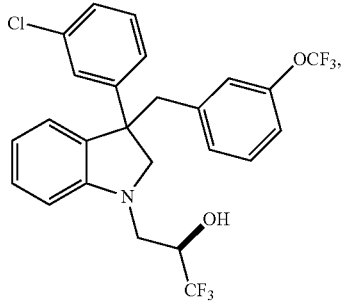

4

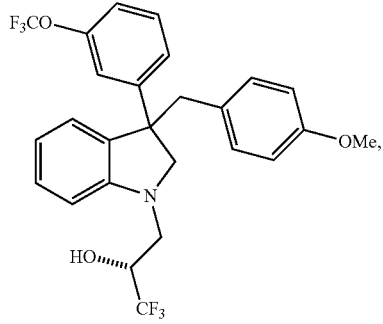

5

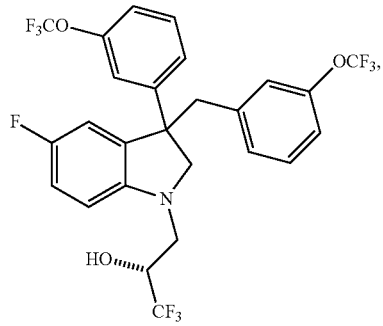

6

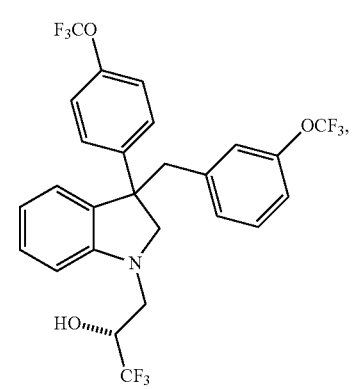
7
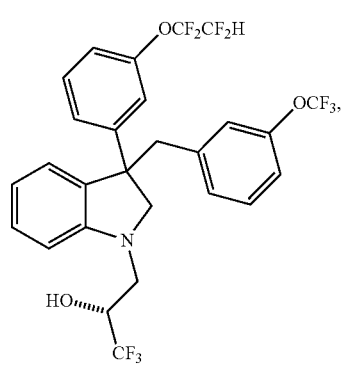
8
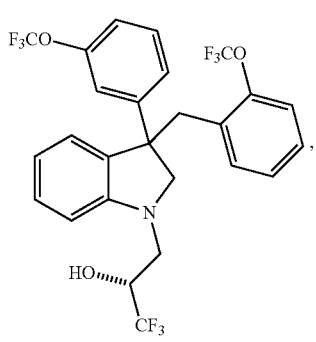
9
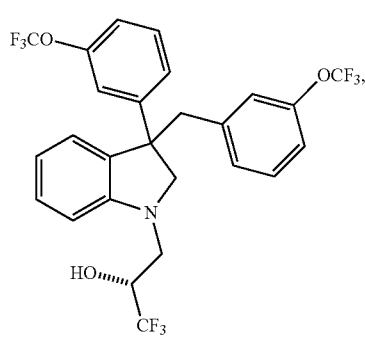
10
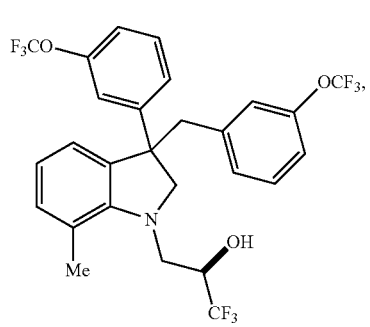
11
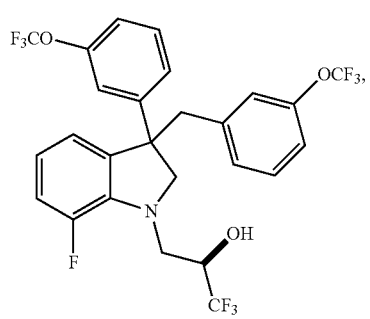
12
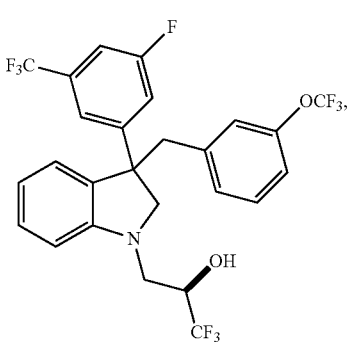
13
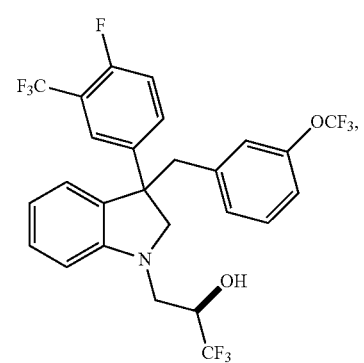
14
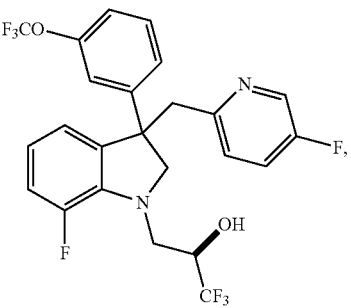
15

-continued
16
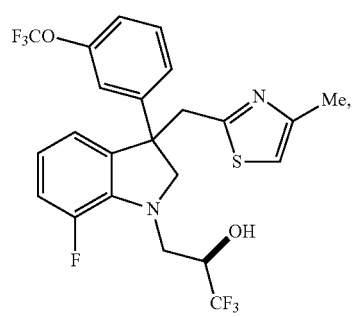
17
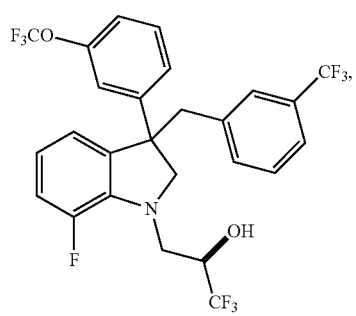
18
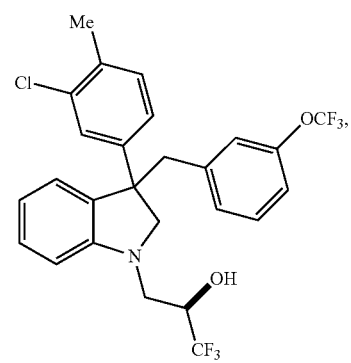
19
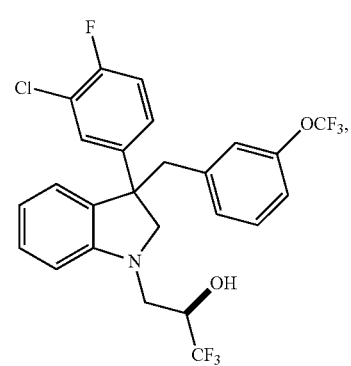
-continued
20
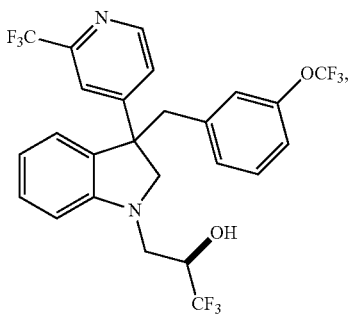
21
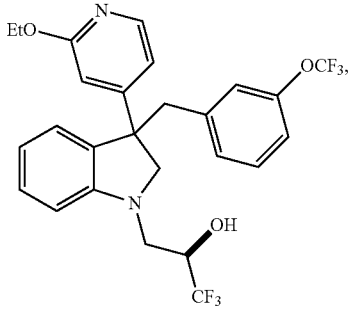
22
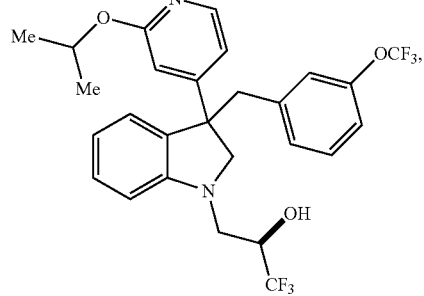
23
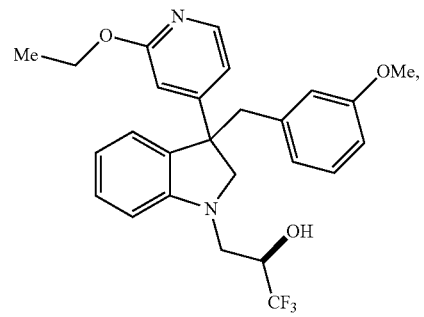
24
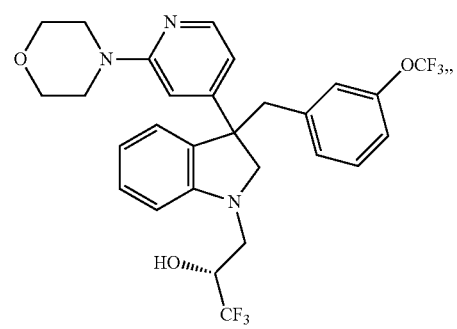

25
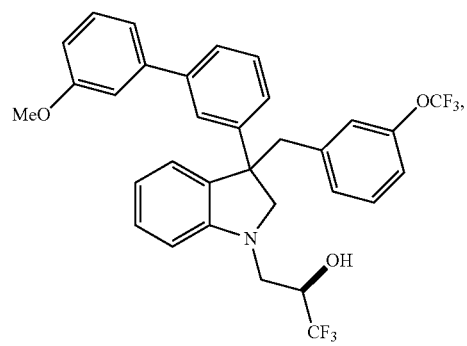
26
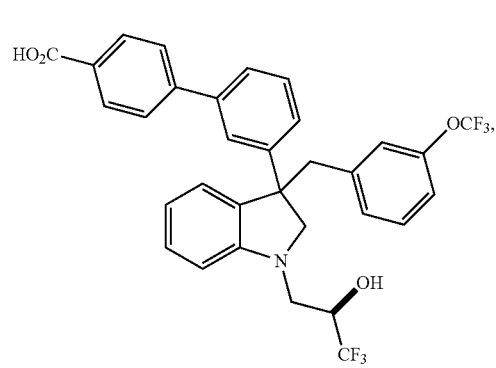
27
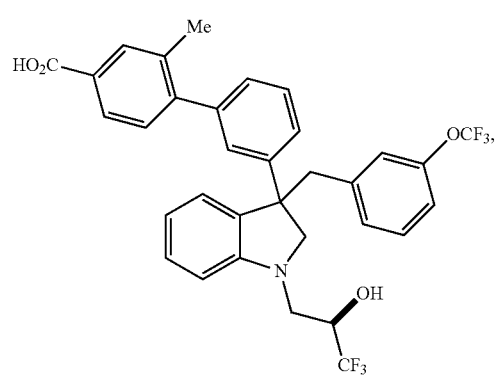
28
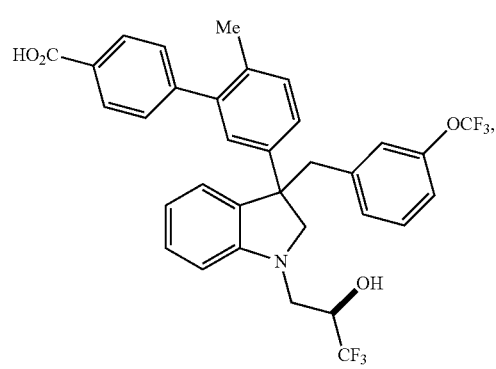
29
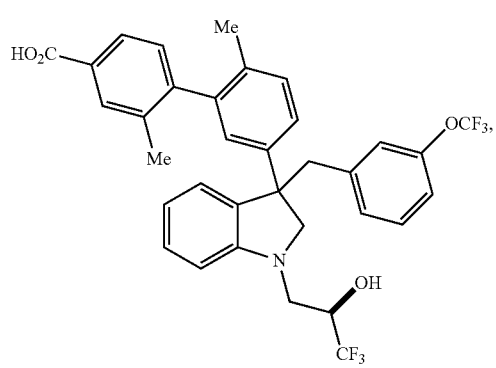
30
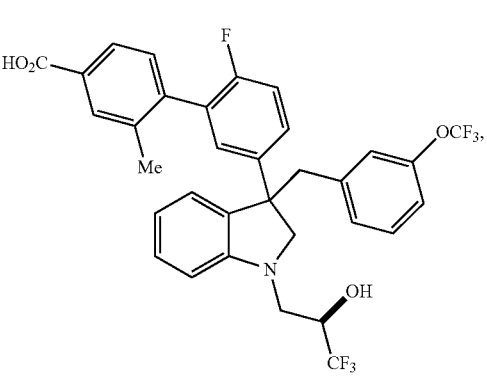
31
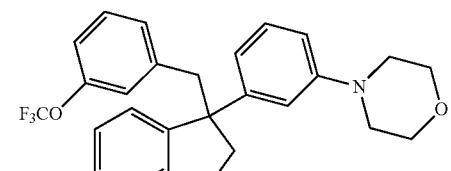
32

33
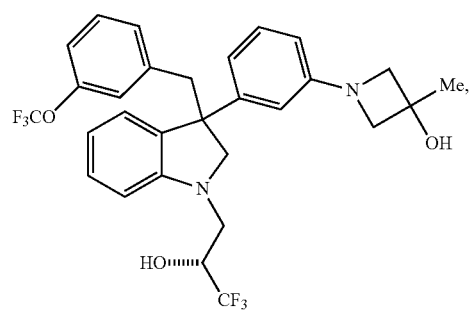
34
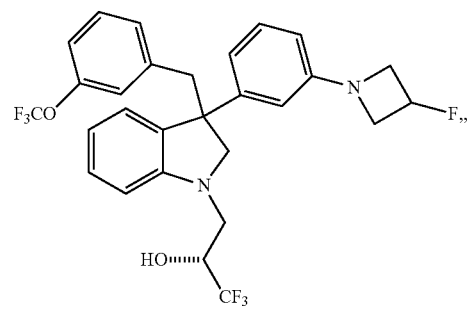
35
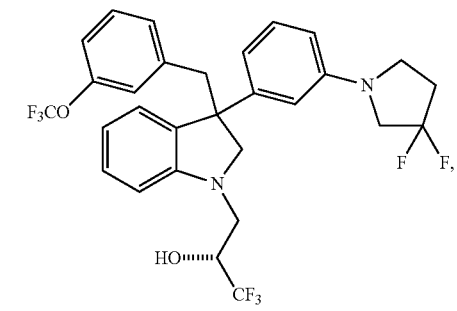
36
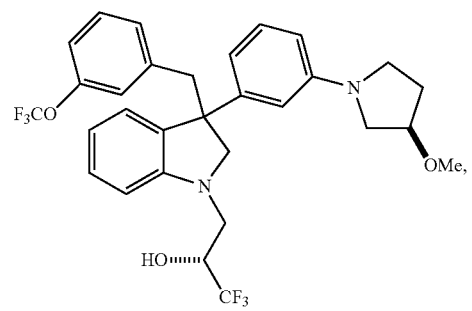
37
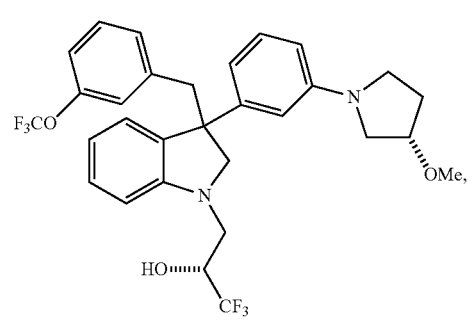
38
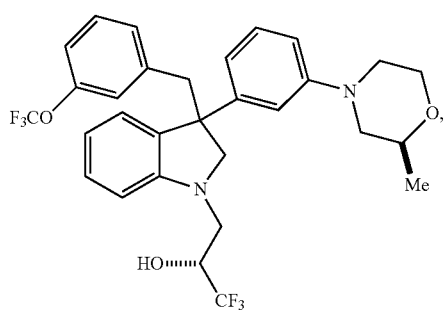
39
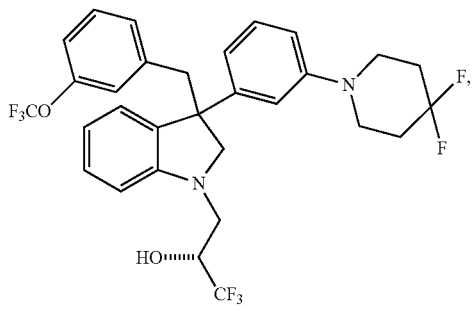
40
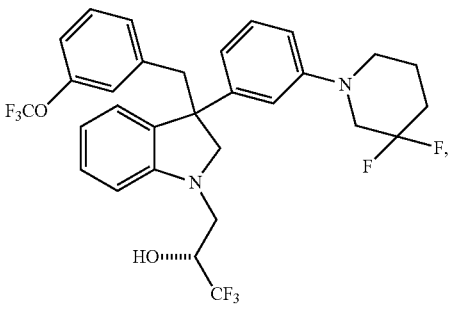
41
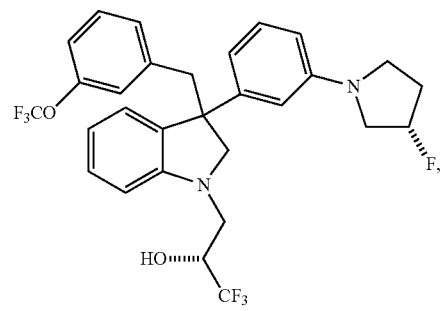
42
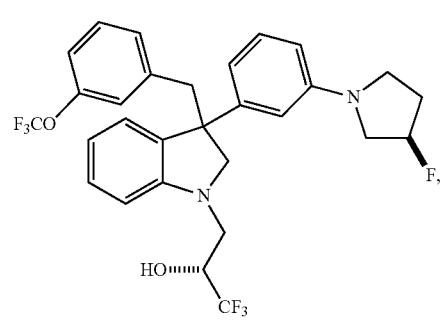

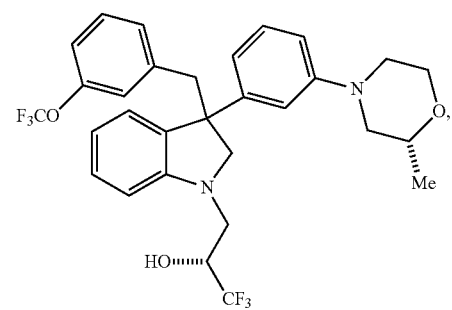
43
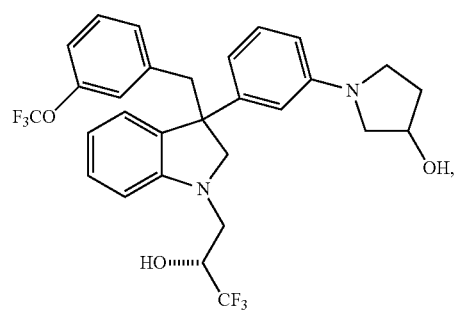
44
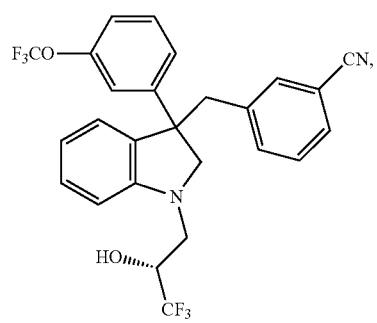
45
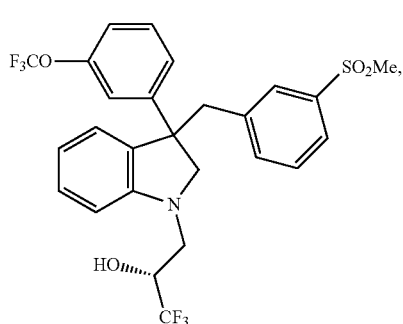
46
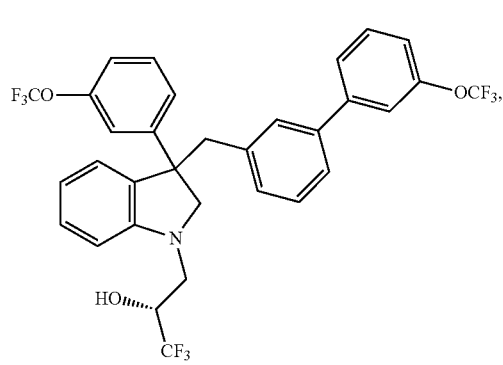
47
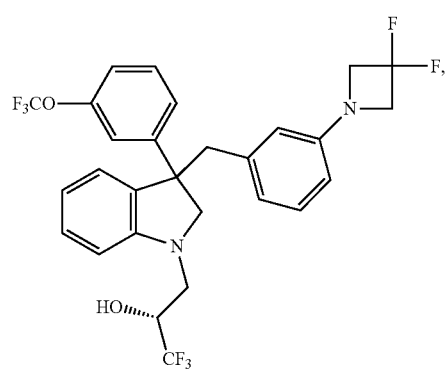
48
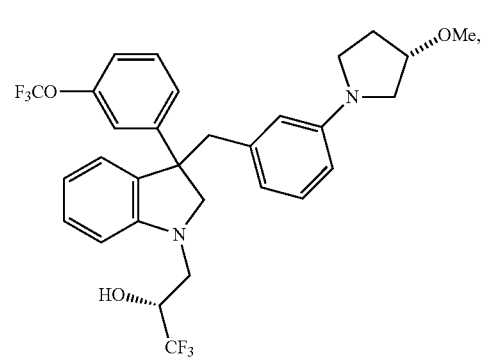
49
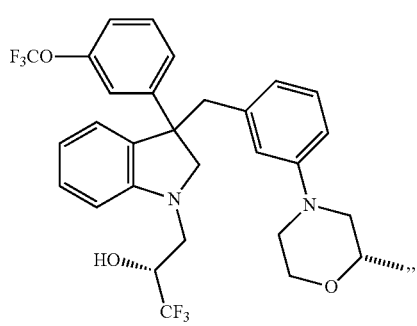
50
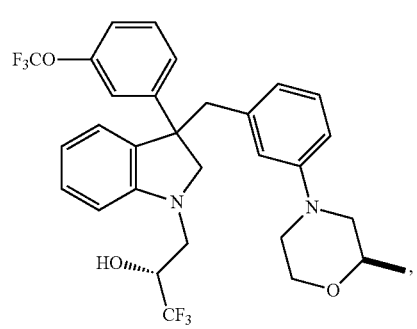
51

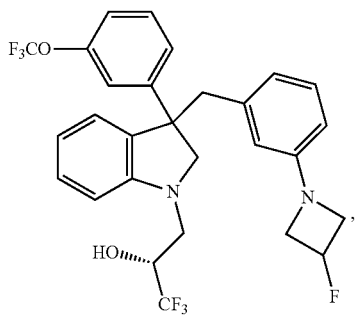

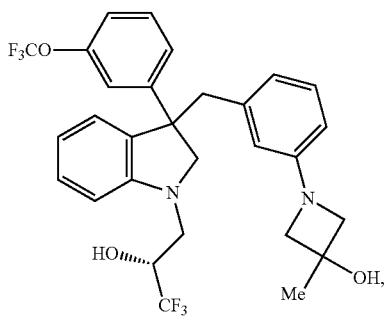

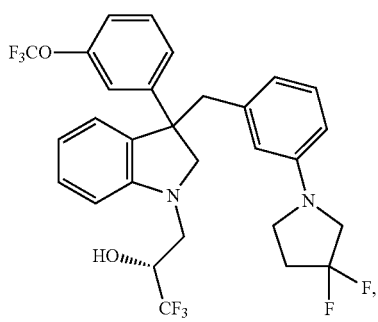

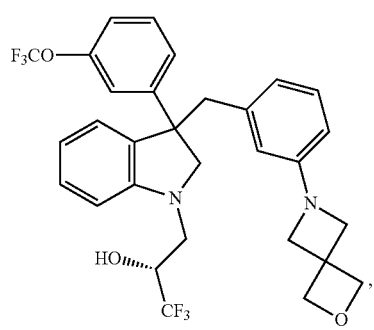

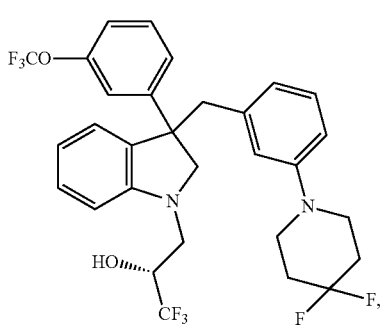

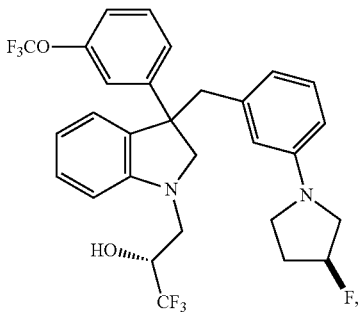

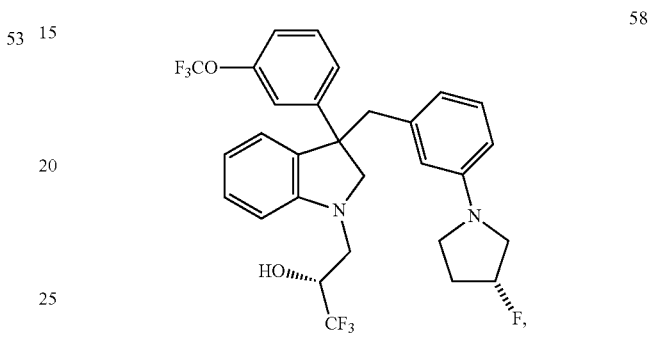

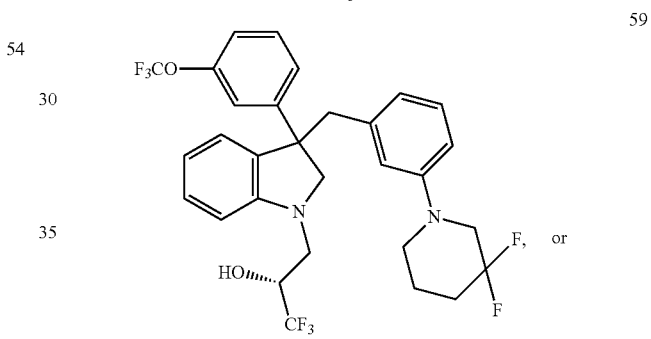

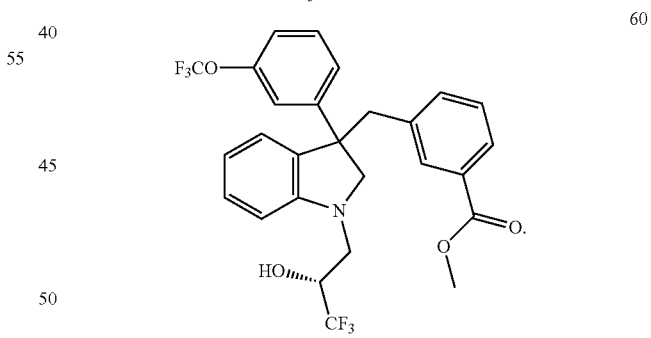

9. A pharmaceutical composition comprising the compound of claim 1, or a pharmaceutically acceptable salt thereof, and a pharmaceutically acceptable carrier.

10. A method of treating atherosclerosis in a patient in need of treatment comprising the administration of a therapeutically effective amount of the compound of claim 1, or a pharmaceutically acceptable salt thereof, to said patient.

11. A method of raising HDL-C in a patient in need of treatment comprising the administration of a therapeutically effective amount of the compound of claim 1, or a pharmaceutically acceptable salt thereof, to said patient.

12. A method of lowering LDL-C in a patient in need of treatment comprising the administration of a therapeutically effective amount of the compound of claim 1, or a pharmaceutically acceptable salt thereof, to said patient.

13. A method of treating dyslipidemia in a patient in need of treatment comprising the administration of a therapeutically effective amount of the compound of claim 1, or a pharmaceutically acceptable salt thereof, to said patient.

14. A pharmaceutical composition comprising the compound of claim 1, or a pharmaceutically acceptable salt thereof, a pharmaceutically acceptable carrier, and one or more active ingredients selected from the group consisting of:
- (i) HMG-CoA reductase inhibitors;
- (ii) bile acid sequestrants;
- (iii) niacin and related compounds; (iv) PPARα agonists;
- (v) cholesterol absorption inhibitors;
- (vi) acyl CoA:cholesterol acyltransferase (ACAT) inhibitors;
- (vii) phenolic anti-oxidants;
- (viii) microsomal triglyceride transfer protein (MTP)/ApoB secretion inhibitors;
- (ix) anti-oxidant vitamins;
- (x) thyromimetics;
- (xi) LDL (low density lipoprotein) receptor inducers;
- (xii) platelet aggregation inhibitors;
- (xiii) vitamin B12 (also known as cyanocobalamin);
- (xiv) folic acid or a pharmaceutically acceptable salt or ester thereof; (xv) FXR and LXR ligands;
- (xvi) agents that enhance ABCA1 gene expression;
- (xvii) ileal bile acid transporters; and
- (xviii) niacin receptor agonists.

15. A pharmaceutical composition comprising the compound of claim 1 or a pharmaceutically acceptable salt thereof, a pharmaceutically acceptable carrier, and an HMG-CoA reductase inhibitor.

* * * * *